(12) United States Patent
Botterbusch et al.

(10) Patent No.: US 11,712,554 B2
(45) Date of Patent: *Aug. 1, 2023

(54) IMPLANTABLE PUMP SYSTEM HAVING A COAXIAL VENTRICULAR CANNULA

(71) Applicant: CorWave SA, Clichy (FR)

(72) Inventors: Carl N. Botterbusch, Wyomissing, PA (US); Silvere Lucquin, Paris (FR); Jean-Baptiste Drevet, Paris (FR); Adrien Guignabert, Meyland (FR); Patrick Meneroud, Vif (FR)

(73) Assignee: CorWave SA, Clichy (FR)

( * ) Notice: Subject to any disclaimer, the term of this patent is extended or adjusted under 35 U.S.C. 154(b) by 37 days.

This patent is subject to a terminal disclaimer.

(21) Appl. No.: 17/409,100

(22) Filed: Aug. 23, 2021

(65) Prior Publication Data

US 2021/0379353 A1    Dec. 9, 2021

Related U.S. Application Data

(60) Division of application No. 16/234,519, filed on Dec. 27, 2018, now Pat. No. 11,097,091, which is a
(Continued)

(51) Int. Cl.
*A61M 60/148* (2021.01)
*A61F 2/82* (2013.01)
(Continued)

(52) U.S. Cl.
CPC ......... *A61M 60/148* (2021.01); *A61F 2/2418* (2013.01); *A61F 2/82* (2013.01);
(Continued)

(58) Field of Classification Search
None
See application file for complete search history.

(56) References Cited

U.S. PATENT DOCUMENTS

| 2,842,067 A | 7/1958 | John et al. |
| 3,107,630 A | 10/1963 | Johnson et al. |

(Continued)

FOREIGN PATENT DOCUMENTS

| AU | 2013203301 A1 | 5/2013 |
| AU | 2013203301 B2 | 10/2015 |

(Continued)

OTHER PUBLICATIONS

Ando, et al., Electrocardiogram-Synchronized Rotational Speed Change Mode in Rotary Pumps Could Improve Pulsatility, Artificial Organs, 35(10):941-947 (2011).
(Continued)

*Primary Examiner* — Catherine M Voorhees
*Assistant Examiner* — Elizabeth K So
(74) *Attorney, Agent, or Firm* — Eversheds Sutherland (US) LLP; Christopher C. Bolten; Robert D. Ward

(57) ABSTRACT

An implantable cardiovascular blood pump system is provided, suitable for use as a left ventricular assist device (LVAD) system, having an implantable cardiovascular pump, an extracorporeal battery and a controller coupled to the implantable pump, and a programmer selectively periodically coupled to the controller to configure and adjust operating parameters of the implantable cardiovascular pump. The implantable cardiovascular blood pump includes a coaxial inflow cannula and outflow cannula in fluid communication with one another and with a pumping mechanism. The pumping mechanism may be a vibrating membrane pump which may include a flexible membrane coupled to an electromagnetic actuator assembly that causes wavelike undulations to propagate along the flexible membrane to propel blood through the implantable cardiovascular pump. The implantable cardiovascular pump may be programmed to operate at frequencies and duty cycles that
(Continued)

mimic physiologic flow rates and pulsatility while avoiding thrombus formation, hemolysis and/or platelet activation.

28 Claims, 20 Drawing Sheets

Related U.S. Application Data continuation of application No. 15/484,108, filed on Apr. 10, 2017, now Pat. No. 10,166,319.

(60) Provisional application No. 62/457,520, filed on Feb. 10, 2017, provisional application No. 62/321,076, filed on Apr. 11, 2016.

(51) Int. Cl.
*A61F 2/24* (2006.01)
*A61M 60/268* (2021.01)
*A61M 60/508* (2021.01)
*A61M 60/462* (2021.01)
*A61M 60/88* (2021.01)
*A61M 60/837* (2021.01)
*A61M 60/859* (2021.01)
*A61M 60/174* (2021.01)

(52) U.S. Cl.
CPC ........ *A61M 60/174* (2021.01); *A61M 60/268* (2021.01); *A61M 60/462* (2021.01); *A61M 60/508* (2021.01); *A61M 60/837* (2021.01); *A61M 60/859* (2021.01); *A61M 60/88* (2021.01)

(56) References Cited

U.S. PATENT DOCUMENTS

| | | |
|---|---|---|
| 3,165,061 A | 1/1965 | Smith et al. |
| 3,608,088 A | 9/1971 | Dorman et al. |
| 3,620,651 A | 11/1971 | Peter |
| 3,743,446 A | 7/1973 | Mandroian |
| 3,765,175 A | 10/1973 | Ohnaka |
| 4,063,826 A | 12/1977 | Riepe |
| 4,277,706 A | 7/1981 | Isaacson |
| 4,384,830 A | 5/1983 | Wakelin |
| 4,484,095 A | 11/1984 | Neumann |
| 4,488,854 A | 12/1984 | Miller |
| 4,498,851 A | 2/1985 | Kolm et al. |
| 4,648,807 A | 3/1987 | Tippetts et al. |
| 4,753,221 A | 6/1988 | Kensey et al. |
| 4,906,229 A | 3/1990 | Wampler |
| 4,918,383 A | 4/1990 | Huff et al. |
| 4,931,036 A | 6/1990 | Kanai et al. |
| 4,939,405 A | 7/1990 | Okuyama et al. |
| 4,955,856 A | 9/1990 | Phillips |
| 4,995,857 A | 2/1991 | Arnold |
| 5,147,388 A | 9/1992 | Yamazaki |
| 5,263,978 A | 11/1993 | Kaufmann et al. |
| 5,275,580 A | 1/1994 | Yamazaki |
| 5,360,445 A | 11/1994 | Goldowsky |
| 5,370,509 A | 12/1994 | Golding et al. |
| 5,525,041 A | 6/1996 | Deak |
| 5,588,812 A | 12/1996 | Taylor et al. |
| 5,840,070 A | 11/1998 | Wampler |
| 5,982,801 A | 11/1999 | Deak |
| 6,030,336 A | 2/2000 | Franchi |
| 6,058,593 A | 5/2000 | Siess |
| 6,079,214 A | 6/2000 | Bishop |
| 6,083,260 A | 7/2000 | Aboul-Hosn |
| 6,116,862 A | 9/2000 | Rau et al. |
| 6,123,725 A | 9/2000 | Aboul-Hosn |
| 6,176,822 B1 | 1/2001 | Nix et al. |
| 6,176,848 B1 | 1/2001 | Rau et al. |
| 6,346,071 B1 | 2/2002 | Mussivand |
| 6,361,284 B2 | 3/2002 | Drevet |
| 6,395,026 B1 | 5/2002 | Aboul-Hosn et al. |
| 6,530,876 B1 | 3/2003 | Spence |
| 6,532,964 B2 | 3/2003 | Aboul-Hosn et al. |
| 6,658,740 B2 | 12/2003 | Habben |
| 6,659,740 B2 | 12/2003 | Drevet |
| 6,672,847 B2 | 1/2004 | Dooley |
| 6,723,039 B2 | 4/2004 | French et al. |
| 6,726,648 B2 | 4/2004 | Kaplon et al. |
| 6,732,501 B2 | 5/2004 | Yu et al. |
| 6,811,381 B2 | 11/2004 | Dooley |
| 6,848,001 B1 | 1/2005 | Sakamoto et al. |
| 6,935,344 B1 | 8/2005 | Aboul-Hosn et al. |
| 6,976,996 B1 | 12/2005 | Aboul-Hosn |
| 7,011,620 B1 | 3/2006 | Siess |
| 7,027,875 B2 | 4/2006 | Siess et al. |
| 7,182,727 B2 | 2/2007 | Aboul-Hosn |
| 7,323,961 B2 | 1/2008 | Drevet |
| 7,520,850 B2 | 4/2009 | Brockway |
| 7,696,634 B2 | 4/2010 | Filardo |
| 7,736,296 B2 | 6/2010 | Siess et al. |
| 7,839,007 B2 | 11/2010 | Filardo |
| 7,863,768 B2 | 1/2011 | Filardo |
| 7,889,877 B2 | 2/2011 | Lutz |
| 7,988,728 B2 | 8/2011 | Ayre |
| 8,012,079 B2 | 9/2011 | Delgado, III |
| 8,152,845 B2 | 4/2012 | Bourque |
| 8,157,720 B2 | 4/2012 | Marseille et al. |
| 8,167,593 B2 | 5/2012 | Gohean et al. |
| 8,333,686 B2 | 12/2012 | Marseille et al. |
| 8,343,029 B2 | 1/2013 | Farnan et al. |
| 8,366,401 B2 | 2/2013 | Pate et al. |
| 8,394,009 B2 | 3/2013 | Bolyard et al. |
| 8,394,010 B2 | 3/2013 | Farnan |
| 8,432,057 B2 | 4/2013 | Filardo |
| 8,449,444 B2 | 5/2013 | Poirier |
| 8,465,410 B2 | 6/2013 | Marseille et al. |
| 8,512,012 B2 | 8/2013 | Akdis et al. |
| 8,550,975 B2 | 10/2013 | Foster |
| 8,556,795 B2 | 10/2013 | Bolyard et al. |
| 8,562,508 B2 | 10/2013 | Dague et al. |
| 8,585,571 B2 | 11/2013 | Bachman et al. |
| 8,597,350 B2 | 12/2013 | Rudser et al. |
| 8,610,304 B2 | 12/2013 | Filardo |
| 8,714,944 B2 | 5/2014 | Drevet |
| 8,753,256 B2 | 6/2014 | Bolyard et al. |
| 8,784,291 B2 | 7/2014 | Farnan et al. |
| 8,821,366 B2 | 9/2014 | Farnan et al. |
| 8,821,527 B2 | 9/2014 | Farnan et al. |
| 8,827,888 B2 | 9/2014 | Bolyard et al. |
| 8,834,136 B2 | 9/2014 | Drevet |
| 8,852,072 B2 | 10/2014 | Larose et al. |
| 8,870,739 B2 | 10/2014 | Larose et al. |
| 8,956,275 B2 | 2/2015 | Bolyard et al. |
| 8,976,546 B2 | 3/2015 | Wang et al. |
| 9,022,916 B2 | 5/2015 | Farnan et al. |
| 9,080,564 B2 | 7/2015 | Drevet |
| 9,089,635 B2 | 7/2015 | Reichenbach et al. |
| 9,144,669 B2 | 9/2015 | Wieselthaler |
| 9,145,875 B2 | 9/2015 | Filardo |
| 9,173,984 B2 | 11/2015 | Larose et al. |
| 9,211,367 B2 | 12/2015 | Farnan et al. |
| 9,308,304 B2 | 4/2016 | Peters et al. |
| 9,446,180 B2 | 9/2016 | Vadala, Jr. et al. |
| 9,526,819 B2 | 12/2016 | Chen |
| 9,572,915 B2 | 2/2017 | Heuring et al. |
| 9,579,437 B2 | 2/2017 | Larose et al. |
| 9,616,158 B2 | 4/2017 | Yaghdjian |
| 9,694,123 B2 | 7/2017 | Bourque et al. |
| 9,731,057 B2 | 8/2017 | Garrigue |
| 9,744,279 B2 | 8/2017 | Tamez et al. |
| 9,786,150 B2 | 10/2017 | Kimball et al. |
| 9,861,728 B2 | 1/2018 | Farnan et al. |
| 9,956,333 B2 | 5/2018 | Larose et al. |
| 9,968,720 B2 | 5/2018 | Botterbusch et al. |
| 10,166,319 B2 | 1/2019 | Botterbusch et al. |
| 10,188,779 B1 | 1/2019 | Polverelli et al. |
| 10,398,821 B2 | 9/2019 | Botterbusch et al. |
| 10,799,625 B2 | 10/2020 | Scheffler et al. |

(56) References Cited

U.S. PATENT DOCUMENTS

| | | |
|---|---|---|
| 10,933,181 B2 | 3/2021 | Le Duc De Lillers et al. |
| 11,097,091 B2 | 8/2021 | Botterbusch et al. |
| 2001/0001278 A1 | 5/2001 | Drevet |
| 2002/0095210 A1 | 7/2002 | Finnegan et al. |
| 2002/0146333 A1 | 10/2002 | Drevet |
| 2002/0165426 A1 | 11/2002 | Sporer et al. |
| 2003/0002325 A1 | 1/2003 | Alvandpour et al. |
| 2004/0002624 A1 | 1/2004 | Yu et al. |
| 2005/0031474 A1 | 2/2005 | Zackl |
| 2005/0261543 A1 | 11/2005 | Abe et al. |
| 2005/0288543 A1 | 12/2005 | Stenberg et al. |
| 2006/0014999 A1 | 1/2006 | Heilman et al. |
| 2006/0155158 A1 | 7/2006 | Aboul-Hosn |
| 2006/0288543 A1 | 12/2006 | Lubera et al. |
| 2007/0299297 A1 | 12/2007 | Jarvik |
| 2008/0232987 A1 | 9/2008 | Drevet |
| 2009/0082778 A1 | 3/2009 | Beane et al. |
| 2010/0234941 A1 | 9/2010 | Finocchiaro et al. |
| 2010/0241223 A1 | 9/2010 | Lee et al. |
| 2011/0124950 A1 | 5/2011 | Foster |
| 2011/0176945 A1 | 7/2011 | Drevet |
| 2011/0176946 A1 | 7/2011 | Drevet |
| 2011/0260449 A1 | 10/2011 | Pokorney |
| 2012/0089225 A1 | 4/2012 | Akkerman et al. |
| 2012/0220816 A1 | 8/2012 | Peters et al. |
| 2012/0323318 A1 | 12/2012 | Yusuf et al. |
| 2013/0042753 A1 | 2/2013 | Becker et al. |
| 2013/0078122 A1 | 3/2013 | Drevet |
| 2013/0178694 A1 | 7/2013 | Jeffery et al. |
| 2013/0267779 A1 | 10/2013 | Woolford et al. |
| 2013/0314047 A1 | 11/2013 | Eagle et al. |
| 2014/0023533 A1 | 1/2014 | Ishii et al. |
| 2014/0187852 A1 | 7/2014 | Peters et al. |
| 2014/0207232 A1 | 7/2014 | Garrigue |
| 2014/0275723 A1 | 9/2014 | Fritz, IV et al. |
| 2014/0277423 A1 | 9/2014 | Alkhatib et al. |
| 2014/0316426 A1 | 10/2014 | Gollner et al. |
| 2015/0167659 A1 | 6/2015 | Sauer |
| 2015/0330383 A1 | 11/2015 | Letailleur et al. |
| 2016/0038664 A1 | 2/2016 | Callaway et al. |
| 2016/0051738 A1 | 2/2016 | Callaway et al. |
| 2016/0235899 A1 | 8/2016 | Yu et al. |
| 2016/0243294 A1 | 8/2016 | Peters et al. |
| 2017/0012491 A1 | 1/2017 | Schob et al. |
| 2017/0266358 A1 | 9/2017 | Aber |
| 2017/0290966 A1 | 10/2017 | Botterbusch et al. |
| 2017/0290967 A1 | 10/2017 | Botterbusch et al. |
| 2017/0296723 A1 | 10/2017 | Garrigue |
| 2018/0038364 A1 | 2/2018 | Dumas et al. |
| 2018/0050143 A1 | 2/2018 | Nguyen et al. |
| 2018/0256798 A1 | 9/2018 | Botterbusch et al. |
| 2018/0369469 A1 | 12/2018 | Le Duc De Lillers et al. |
| 2019/0125949 A1 | 5/2019 | Botterbusch et al. |
| 2019/0381227 A1 | 12/2019 | Botterbusch et al. |
| 2020/0368417 A1 | 11/2020 | Polverelli et al. |
| 2021/0170160 A1 | 6/2021 | Le Duc De Lillers et al. |
| 2021/0172429 A1 | 6/2021 | Drevet et al. |

FOREIGN PATENT DOCUMENTS

| | | |
|---|---|---|
| CA | 2712945 A1 | 7/2009 |
| CN | 1257006 A | 6/2000 |
| CN | 1355715 A | 6/2002 |
| CN | 1714759 A | 1/2006 |
| CN | 101472627 A | 7/2009 |
| CN | 101878049 A | 11/2010 |
| CN | 102112744 A | 6/2011 |
| CN | 106421939 A | 2/2017 |
| CN | 106489026 A | 3/2017 |
| EP | 0412856 A1 | 2/1991 |
| EP | 0415949 A1 | 3/1991 |
| EP | 0412856 B1 | 1/1994 |
| EP | 0445782 B1 | 8/1994 |
| EP | 0925081 B1 | 12/2003 |
| EP | 0961621 B1 | 7/2004 |
| EP | 1551500 A2 | 7/2005 |
| EP | 1233797 B1 | 7/2006 |
| EP | 1337288 B1 | 3/2008 |
| EP | 1981585 A2 | 10/2008 |
| EP | 1644639 B1 | 2/2009 |
| EP | 2152339 A1 | 2/2010 |
| EP | 2249746 A1 | 11/2010 |
| EP | 2310067 A1 | 4/2011 |
| EP | 2600918 A1 | 6/2013 |
| EP | 2517739 B1 | 12/2013 |
| EP | 2704761 A1 | 3/2014 |
| EP | 2310067 B1 | 4/2014 |
| EP | 2753389 A1 | 7/2014 |
| EP | 2152339 B1 | 5/2015 |
| EP | 2891502 A1 | 7/2015 |
| EP | 2704761 B1 | 9/2015 |
| EP | 2736552 B1 | 9/2015 |
| EP | 2891502 B1 | 7/2016 |
| EP | 2164542 B1 | 8/2016 |
| EP | 2856190 B1 | 9/2016 |
| EP | 3145558 A2 | 3/2017 |
| FR | 355700 A | 11/1905 |
| FR | 2650862 B1 | 11/1991 |
| FR | 2744769 A1 | 8/1997 |
| FR | 2744769 B1 | 2/1999 |
| FR | 2861910 B1 | 1/2006 |
| FR | 2905147 A1 | 2/2008 |
| FR | 3032917 A1 | 8/2016 |
| GB | 662047 A | 11/1951 |
| JP | 2011509801 A | 3/2011 |
| KR | 20130068373 A | 6/2013 |
| WO | WO-8910763 A1 | 11/1989 |
| WO | WO-9008260 A1 | 7/1990 |
| WO | WO-9729282 A1 | 8/1997 |
| WO | WO-9959652 A1 | 11/1999 |
| WO | WO-2007053881 A1 | 5/2007 |
| WO | WO-2011056823 A2 | 5/2011 |
| WO | WO-2016179262 A1 | 11/2016 |
| WO | WO-2017087717 A1 | 5/2017 |
| WO | WO-2017087785 A1 | 5/2017 |
| WO | WO-2019092175 A1 | 5/2019 |
| WO | WO-2020115607 A2 | 6/2020 |

OTHER PUBLICATIONS

Ando, et al., Left ventricular decompression through a patent foramen ovale in a patient with hypertrophic cardiomyopathy: A case report, Cardiovascular Ultrasound, 2: 1-7 (2004).

Bozkurt, et al., Improving Arterial Pulsatility by Feedback Control of a Continuous Flow Left Ventricular Assist Device via in silico Modeling, International Journal of Artificial Organs, 37(10):773-785 (2014).

Castellanos, et al., Generations of Left Ventricular Assist Devices: The HeartMate Family, Dept. of Bioengineering. Florida Gulf Coast University, BME 3100C, pp. 1-6. (No date available).

Crow, et al., Gastrointestinal Bleeding Rates in Recipients of Nonpulsatile and Pulsatile Left Ventricular Assist Devices, The Journal of Thoracic and Cardiovascular Surgery, 137(1):208-215 (2009).

Fatullayev, et al., Continuous-Flow Left Ventricular Assist Device Thrombosis: A Danger Foreseen is a Danger Avoided, Medical Science Monitor Basic Research, 21:141-144 (2015).

Feier, et al., A Novel, Valveless Ventricular Assist Device: The Fish Tail Pump. First Experimental in Vivo Studies, Artificial Organs, (26)12:1026-1031 (2002).

Fliess, et al., Flatness and Defect of Nonlinear Systems: Introductory Theory and Examples, International Journal of Control, 61(6):1327-1361 (1995).

Fraser et al., A Quantitative Comparison of Mechanical Blood Damage Parameters in Rotary Ventricular Assist Devices: Shear Stress, Exposure Time and Hemolysis Index, Journal of Biomechanical Engineering, 134(8):018002-1 to 018002-11 (2012).

Harris, et al., Ventricular Assist Devices, Continuing Education in Anesthesia, Critical Care & Pain, 12(3):145-151 (2012).

International Search Report & Written Opinion dated Mar. 4, 2019 in Int'l PCT Patent Appl. No. PCT/IB2018/059199, 13 pages.

(56) References Cited

OTHER PUBLICATIONS

International Search Report & Written Opinion dated May 14, 2021 in Int'l PCT Patent Appl. Serial No. PCT/IB2021/051879.
International Search Report & Written Opinion dated Jun. 28, 2017 in Int'l PCT Patent Application Serial No. PCT/IB2017/052068.
International Search Report & Written Opinion dated Jul. 15, 2020 in Int'l PCT Patent Appl. Serial No. PCT/IB2019/060144.
International Search Report & Written Opinion dated Aug. 22, 2017 in Int'l PCT Patent Application Serial No. PCT/IB2017/052069.
International Search Report and Written Opinion dated Apr. 16, 2019 in Int'l. PCT Patent Appl. Serial No. PCT/EP2018/080749 (English Translation of ISR only).
International Search Report and Written Opinion dated Jun. 25, 2020 in International PCT Patent Application Serial No. PCT/IB2020/052337.
International Search Report and Written Opinion dated Aug. 3, 2018 in Int'l PCT Patent Appl. Serial No. PCT/IB2018/052215.
Ising, M., RPM and Flow Modulation for a Continuous Flow Left Ventricular Assist Device to Increase Vascular Pulsatility: A Computer Simulation, Mock Circulation, and In-Vivo Animal Study, University of Louisville, Think IR: The University of Louisville's Institutional Repository, Electronic Theses and Dissertations (Jul. 2011).
Islam et al., Left Ventricular Assist Devices and Gastrointestinal Bleeding: A Narrative Review of Case Reports and Case Series, Clinical Cardiology, 36(4):190-200 (2013).
Jorde, et al., Identification and Management of Pump Thrombus in the HeartWare Left Ventricular Assist Device System, JACC: Heart Failure, 3(11):849-856 (2015).
Latham, et al., Parameter Estimation and a Series of Nonlinear Observers for the System Dynamics of a Linear Vapor Compressor, IEEE Transactions on Industrial Electronics, 63(11):6736-6744 (2016).
Leverett, et al., Red Blood Cell Damage by Shear Stress, Biophysical Journal, 12(3):257-273 (1972).
Malehsa, et al., Acquired von Willebrand Syndrome After Exchange of the HeartMate XVE to the HeartMate II Ventricular Assist Device, European Journal of Cardio-Thoracic Surgery, 35(6):1091-1093 (2009).
Mancini, et al., Left Ventricular Assist Devices, A Rapidly Evolving Alternative to Transplant, Journal of the American College of Cardiology, 653:2542-2555 (2015).
Mboup, et al., Numerical Differentiation With Annihilators in Noisy Environment, Numerical Algorithms, 50(4):439-467 (2009).
Menhour, et al., An Efficient Model-Free Setting for Longitudinal and Lateral Vehicle Control: Validation Through the Interconnected Pro-SiVIC/RTMaps Prototyping Platform, IEEE Transactions on Intelligent Transportation Systems, 19(2):461-475 (2018).
Mercorelli, P., A Motion-Sensorless Control for Intake Valves in Combustion Engines, IEEE Transactions on Industrial Electronics, 64(4):3402-3412 (2017).
Mercorelli, P., An Adaptive and Optimized Switching Observer for Sensorless Control of an Electromagnetic Valve Actuator in Camless Internal Combustion Engines, Asian Journal of Control, 16(4):959-973 (2014).
Mohite, et al., Does CircuLite Synergy Assist Device as Partial Ventricular Support have a Place in Modern Management of Advanced Heart Failure?, Expert Rev. Med. Devices, published online Dec. 2, 2014 (pp. 1-12).
Najjar, et al., An Analysis of Pump Thrombus Events in Patients in HeartWare Advance Bridge to Transplant and Continued Access Protocol Trial, The Journal of Heart and Lung Transplantation, 33(1):23-34 (2014).
Pagani, Francis D., MD, PhD, Department of Cardiac Surgery, University of Michigan, "Technology 101: Review of Current Technologies, Types of Flow, Pump Parameters," American Association for Thoracic Surgery, Annual Meeting (2014), Cardiothoracic Transplant and Mechanical Circulatory Support of Heart and Lung Failure.
Perschall, et al., The Progressive Wave Pump: Numerical Multiphysics Investigation of a Novel Pump Concept With Potential to Ventricular Assist Device Application, Artificial Organs, 35(9):E179-E190 (2012).
Rahman, et al., Position Estimation in Solenoid Actuators, IEEE Transactions on Industry Applications, 32(3):552-559 (1996).
Rigatos, G., Differential Flatness Theory ad Flatness-Based Control, in Nonlinear Control and Filtering Using Differential Flatness Approaches, 25(2):47-101 (2015).
Wang, et al., Rotary Blood Pump Control Strategy for Preventing Left Ventricular Suction, ASAIO Journal, 61(1):21-30(2015).
Wang., Quadrotor Analysis and Model Free Control with Comparisons, Universite Paris Sud—Paris XI, (2013).
Weidemann, Daniel., Thesis entitled, Permanent Magnet Reluctance Actuators for Vibration Testing, Completed at the Institute of Applied Mechanics, Technische Universitat Munchen, Apr. 2013.
Yuan, et al., The Spectrum of Complications Following Left Ventricular Assist Device Placement, Journal of Cardiac Surgery, 27:630-638 (2012).
Zhang, et al., Study on Self-Sensor of Linear Moving Magnet Compressor's Piston Stroke, IEEE Sensors Journal, 9(2):154-158 (2009).
U.S. Appl. No. 15/484,101 / U.S. Pat. No. 9,968,720, filed Apr. 10, 2017 / May 15, 2018.
U.S. Appl. No. 15/484,108 / U.S. Pat. No. 10,166,319, filed Apr. 10, 2017 / Jan. 1, 2019.
U.S. Appl. No. 15/940,856 / U.S. Pat. No. 10,933,181, filed Mar. 29, 2018 / Mar. 2, 2021.
U.S. Appl. No. 15/953,269 / U.S. Pat. No. 10,188,779, filed Apr. 13, 2018 / Jan. 29, 2019.
U.S. Appl. No. 15/976,831 / U.S. Pat. No. 10,398,821, filed May 10, 2018 / Sep. 3, 2019.
U.S. Appl. No. 16/234,519 / U.S. Pat. No. 11,097,091, filed Dec. 27, 2018 / Aug. 24, 2021.
U.S. Appl. No. 16/557,711, filed Aug. 30, 2019.
U.S. Appl. No. 16/762,909, filed May 8, 2019.
U.S. Appl. No. 16/766,267, filed May 21, 2020.
U.S. Appl. No. 16/819,021 / U.S. Pat. No. 10,799,625, filed Mar. 13, 2020 / Oct. 31, 2020.
U.S. Appl. No. 17/179,961, filed Feb. 19, 2021.
U.S. Appl. No. 17/193,867, filed Mar. 5, 2021.
U.S. Appl. No. 17/299,749, filed Jun. 3, 2021.
Extended European Search Report dated Aug. 25, 2021 in EP Patent Application Serial No. 21168340.4.

IMPLANTABLE PUMP SYSTEM HAVING A COAXIAL VENTRICULAR CANNULA

CROSS-REFERENCE TO RELATED APPLICATIONS

This application is a divisional application of U.S. patent application Ser. No. 16/234,519, filed Dec. 27, 2018, now U.S. Pat. No. 11,097,091, which is a continuation application of U.S. patent application Ser. No. 15/484,108, filed Apr. 10, 2017, now U.S. Pat. No. 10,166,319, which claims the benefit of the filing dates of U.S. Provisional Patent Application Nos. 62/321,076 filed on Apr. 11, 2016, and 62/457,520, filed on Feb. 10, 2017, the entire contents of each of which are incorporated herein by reference.

FIELD OF THE INVENTION

The present invention relates generally to heart pumps and more particularly to implantable heart pumps having coaxial ventricular cannulas.

BACKGROUND

The human heart is comprised of four major chambers with two ventricles and two atria. Generally, the right-side heart receives oxygen-poor blood from the body into the right atrium and pumps it via the right ventricle to the lungs. The left-side heart receives oxygen-rich blood from the lungs into the left atrium and pumps it via the left ventricle to the aorta for distribution throughout the body. Due to any of a number of illnesses, including coronary artery disease, high blood pressure (hypertension), valvular regurgitation and calcification, damage to the heart muscle as a result of infarction or ischemia, myocarditis, congenital heart defects, abnormal heart rhythms or various infectious diseases, the left ventricle may be rendered less effective and thus unable to adequately pump oxygenated blood throughout the body.

The Centers for Disease Control and Prevention (CDC) estimates that about 5.1 million people in the United States suffer from some form of heart failure. Heart failure is generally categorized into four different stages with the most severe being end stage heart failure. End stage heart failure may be diagnosed where a patient has heart failure symptoms at rest in spite of medical treatment. Patients at this stage may have systolic heart failure, characterized by decreased ejection fraction. In patients with systolic heart failure, the walls of the ventricle are weak and do not squeeze as forcefully as a healthy patient. Consequently, during systole a reduced volume of oxygenated blood is ejected into circulation, a situation that continues in a downward spiral until death. Patients may alternatively have diastolic heart failure wherein the heart muscle becomes stiff or thickened making it difficult for the affected chamber to fill with blood. A patient diagnosed with end stage heart failure has a one-year mortality rate of approximately 50%.

For patients that have reached end stage heart failure, treatment options are limited. In addition to continued use of drug therapy commonly prescribed during earlier stages of heart failure, cardiac transplantation and implantation of a mechanical assist device are typically recommended. While a cardiac transplant may significantly prolong the patient's life beyond the one year mortality rate, patients frequently expire while on a waitlist for months and sometimes years awaiting a suitable donor heart. Presently, the only alternative to a cardiac transplant is a mechanical implant. While in recent years mechanical implants have improved in design, typically such implants will prolong a patient's life by a few years at most, and include a number of co-morbidities.

One type of mechanical implant often used for patients with end stage heart failure is a left ventricular assist device (LVAD). The LVAD is a surgically implanted pump that draws oxygenated blood from the left ventricle and pumps it directly to the aorta, thereby off-loading (reducing) the pumping work of the left ventricle. LVADs typically are used either as "bridge-to-transplant therapy" or "destination therapy." When used for bridge-to-transplant therapy, the LVAD is used to prolong the life of a patient who is waiting for a heart transplant. When a patient is not suitable for a heart transplant, the LVAD may be used as a destination therapy to prolong the life, or improve the quality of life, of the patient, but generally such prolongation is for only a couple years.

One type of LVAD is a reciprocating pump such as U.S. Pat. No. 4,277,706 to Isaacson, entitled "Actuator for Heart Pump." The pump described in the Isaacson patent includes a housing having an inlet and an outlet, a cavity in the interior of the pump connected to the inlet and the outlet, a flexible diaphragm that extends across the cavity, a plate secured to the diaphragm, and a ball screw that is configured to be reciprocated to drive the plate and connected diaphragm from one end of the cavity to the other end to simulate systole and diastole. The ball screw is actuated by a direct current motor. The Isaacson patent also describes a controller configured to manage the revolutions of the ball screw to control the starting, stopping and reversal of directions to control blood flow in and out of the pump.

LVADs utilizing rotary, centrifugal and axial configurations also are known. For example, U.S. Pat. No. 3,608,088 to Reich, entitled "Implantable Blood Pump," describes a centrifugal pump to assist a failing heart. The Reich patent describes a centrifugal pump having an inlet connected to a rigid cannula that is coupled to the left ventricular cavity and a Dacron graft extending from the pump diffuser to the aorta. The pump includes an impeller that is rotated at high speeds to accelerate blood, and simulated pulsations of the natural heart by changing rotation speeds or introducing a fluid oscillator.

U.S. Pat. No. 5,370,509 to Golding, entitled "Sealless Rotodynamic Pump with Fluid Bearing," describes a centrifugal blood pump capable for use as a heart pump. One embodiment described involves a blood pump with impeller blades that are aligned with the axes of the blood inlet and blood outlet. U.S. Pat. No. 5,588,812 to Taylor, entitled "Implantable Electrical Axial-Flow Blood Pump," describes an axial flow blood pump. The pump described in the Taylor patent has a pump housing that defines a cylindrical blood conduit through which blood is pumped from the inlet to the outlet, and rotor blades that rotate along the axis of the pump to accelerate blood flowing through the blood conduit.

Pumps other than the rotary and positive displacement types are known in the art for displacing fluid. For example, U.S. Pat. Nos. 6,361,284 and 6,659,740, both to Drevet, entitled "Vibrating Membrane Fluid Circulator," describe pumps in which a deformable membrane is vibrated to propel fluid through a pump housing. In these patents, vibratory motion applied to the deformable membrane causes wave-like undulations in the membrane that propel the fluid along a channel. Different flow rates may be achieved by controlling the excitation applied to the membrane.

U.S. Pat. No. 7,323,961 to Drevet, entitled "Electromagnetic Machine with a Deformable Membrane", describes a device in which a membrane is coupled in tension along its outer edge to an electromagnetic device arranged to rotate about the outer edge of the membrane. As the electromagnetic device rotates, the outer edge of the membrane is deflected slightly in a direction normal to the plane of the membrane. These deflections induce a wave-like undulation in the membrane that may be used to move a fluid in contact with the membrane.

U.S. Pat. No. 9,080,564 to Drevet, entitled "Diaphragm Circulator," describes a tensioned deformable membrane in which undulations are created by electromechanically moving a magnetized ring, attached to an outer edge of a deformable membrane, over a coil. Axial displacement of magnetized ring causes undulations of membrane. Like in the '961 patent, the membrane undulations can be controlled by manipulating the magnetic attraction. U.S. Pat. No. 8,714,944 to Drevet, entitled "Diaphragm pump with a Crinkle Diaphragm of Improved Efficiency" and U.S. Pat. No. 8,834,136 to Drevet, entitled "Crinkle Diaphragm Pump" teach similar types of vibrating membrane pumps.

Notwithstanding the type of LVAD device employed, an LVAD generally includes an inflow cannula, a pump, and an outflow cannula, and is coupled to an extracorporeal battery and control unit. The inflow cannula typically directly connects to the left ventricle, e.g., at the apex, and delivers blood from the left ventricle to the pump. The outflow cannula typically extends outside of the heart and includes an extra-cardiac return line that is routed through the upper chest and connects to the aorta distal to the aortic valve. As such the outflow cannula delivers blood from the pump to the aorta via the return line, which typically consists of a tubular structure, such as a Dacron graft, that is coupled to the aorta via an anastomosis.

A sternotomy or thoracotomy is required to implant the pump within the patient. In addition, a separate aortic anastomosis procedure is also required to connect the pump to the aorta. The return line that delivers oxygen-rich blood to the aorta significantly reduces efficiency of the system. Additionally, when the pump is operated in a pulsatile mode the return line that connects the pump to the aorta should incorporate an artificial valve or require the pump to run continually to prevent backflow, thus increasing the risk of barotrauma to the blood. The return line also creates issues with possible kinking caused by chest compression. The increased foreign surface area of the return line also can lead to undesired platelet activation and thrombosis.

What is needed is an energy efficient implantable pump having light weight, small size, and a delivery mechanism for delivering blood to the aorta with minimal blood damage.

SUMMARY OF THE INVENTION

The present invention overcomes the drawbacks of previously-known LVAD systems and methods by providing an implantable cardiovascular blood pump system having coaxial cannulas and an undulating membrane capable of producing a wide range of physiological flow rates while applying low shear forces to the blood, thereby reducing hemolysis and platelet activation relative to previously-known systems. The coaxial cannulas permit blood to pump from the left ventricle to the aorta without the need for a return line extending along the exterior of the heart from the left ventricle to the aorta.

In accordance with one aspect of the invention, the implantable cardiovascular pump system may include, in addition to a cardiovascular pump, a controller, a battery, a programmer and a software module programmed to run on a mobile device. The cardiovascular pump may include a vibrating membrane pump assembly contained within a pump housing that may be implanted in a patient's heart. The vibrating membrane pump assembly may have a vibrating membrane that may also be disposed with the pump housing. An outflow cannula having an inlet and an outlet, and an inflow cannula having an inlet and an outlet may be in fluid communication with the vibrating membrane pump assembly. The outflow cannula may be disposed coaxially within the inflow cannula. In operation the vibrating membrane may vibrate to pump blood from the inlet of the inflow cannula, through the pump housing and out the outlet of the outflow cannula.

The inflow cannula may be coupled to the pump housing at an outlet and may have an inlet inserted into a left ventricle. The pump may also have an outflow cannula with an outlet that is also inserted into the left ventricle and an inlet that is in fluid communication with the pump. In other embodiments the pump housing, the outflow cannula and the inflow cannula may be implanted within the left ventricle of a patient.

The outflow cannula of the pump may be coupled to an intraventricular outflow conduit that extends from the outflow cannula. One end of the outflow conduit may be positioned through the aortic valve and may be sized and shaped to permit the aortic valve to open and close around the outflow conduit. Alternatively, the outflow conduit may be coupled at one end to the outflow cannula and at the other end extend within the left ventricle to a stent mounted valve anchored to the aortic valve. In yet another alternative configuration, the outflow conduit may terminate before reaching the aortic valve. Where the outflow conduit terminates before reaching the aortic valve, the outflow conduit may be suspended in the left ventricle and oriented toward the aortic valve. To secure the outflow conduit in an orientation toward the aortic valve, the outflow conduit may be anchored to the left ventricular outflow tract.

The vibrating membrane pump may also include an actuator assembly disposed within the cylindrical pump housing with an electromagnet assembly for selectively generating a magnetic field. A magnet ring may be concentrically suspended around the actuator assembly and may move towards or away from the electromagnet assembly responsive to the magnetic field. The magnet ring may be coupled to the membrane assembly and cause the membrane assembly to vibrate as it moves.

Methods and systems for pumping blood using the implantable cardiovascular blood pump system having coaxial cannulas are provided.

DETAILED DESCRIPTION

The implantable cardiovascular pump system of the present invention includes a pump, a controller, a battery, a programmer and may include a mobile device. The pump may be any pump particularly well-suited for use as a left ventricular assist device (LVAD), including for example, a vibrating membrane pump, an axial flow pump, a centrifugal pump and a reciprocating pump. The pump includes a cylindrical pump housing and an inflow cannula and an outflow cannula that are arranged in a coaxial manner. The outflow cannula is sized to fit within the inflow cannula and may extend beyond the inflow cannula or in some embodiments terminate before or at the inflow cannula.

Figure 1:
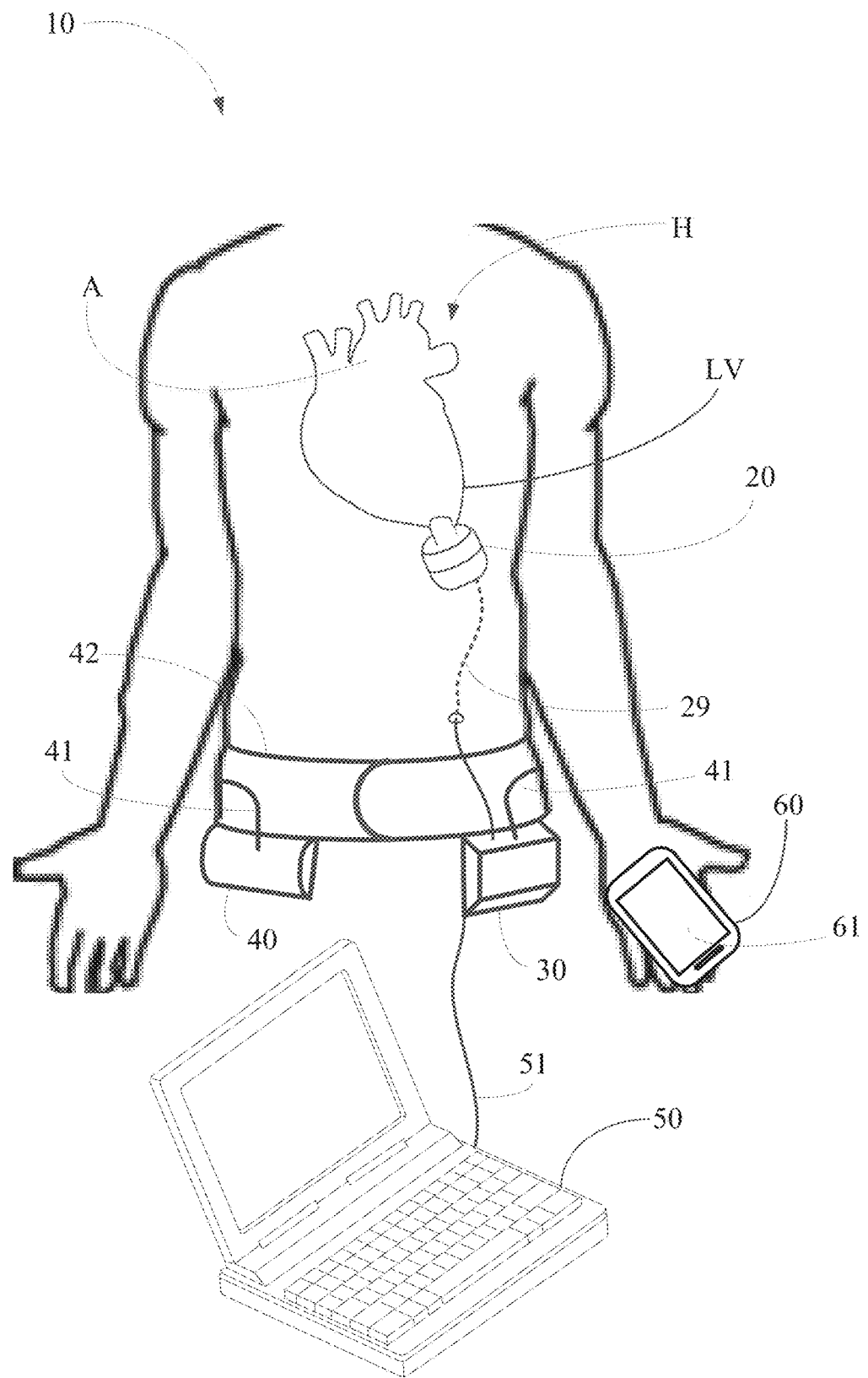
FIG. 1 depicts an exemplary embodiment of the blood pump system of the present invention comprising an implantable blood pump, controller, battery, programmer and mobile device.

Referring now to FIG. 1, pump system 10 constructed in accordance with the principles of the present invention is described. Pump system 10 includes implantable pump 20, controller 30, battery 40, programmer 50 and optionally, a software module programmed to run on mobile device 60. Implantable pump 20 may be configured to be implanted within a patient's chest through a thoracotomy. Implantable pump 20 may be affixed to the heart using a ring-suture or other conventional technique.

Figure 2:
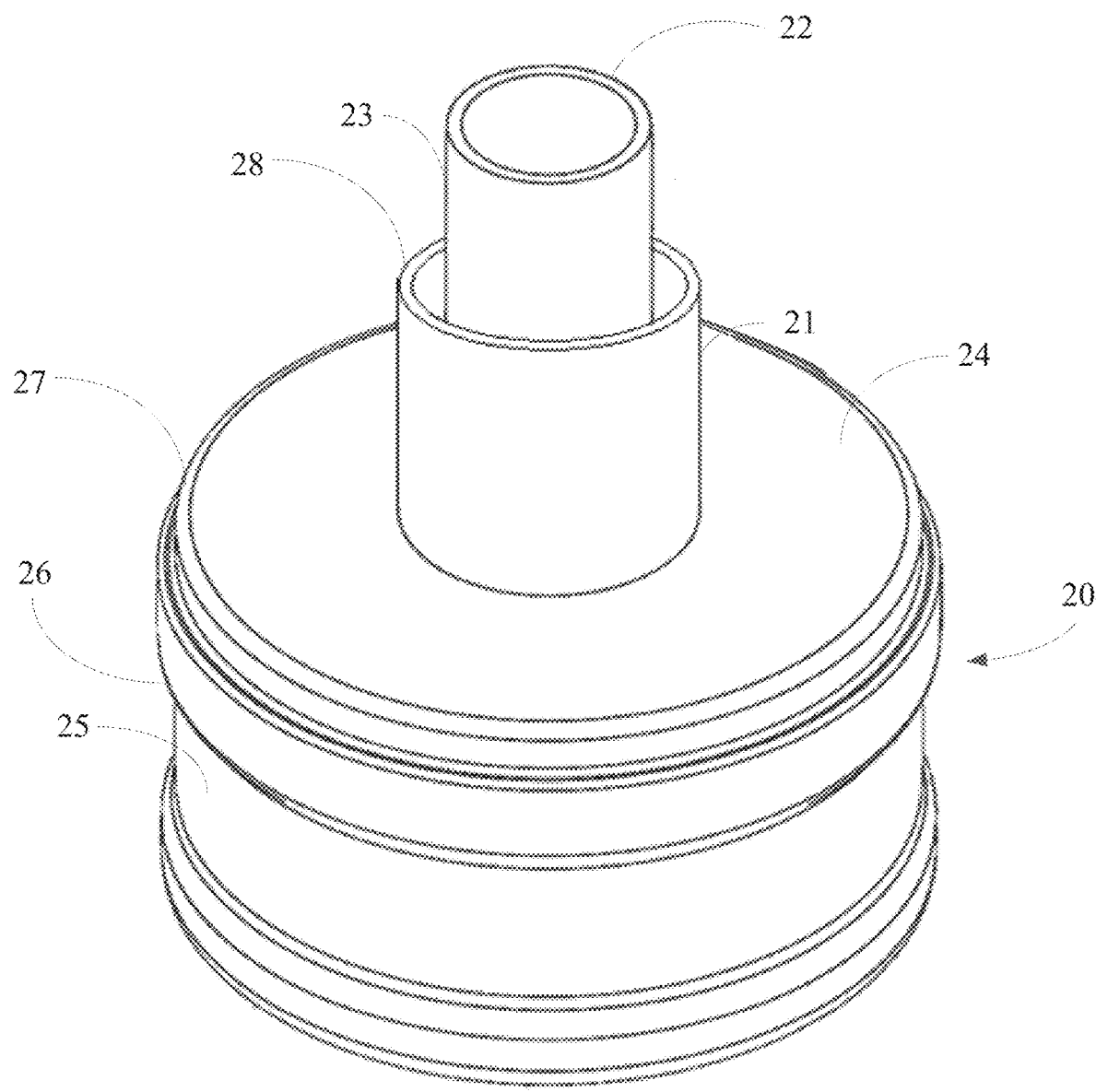
FIG. 2 is a perspective view of the implantable pump of FIG. 1.
Figure 6:
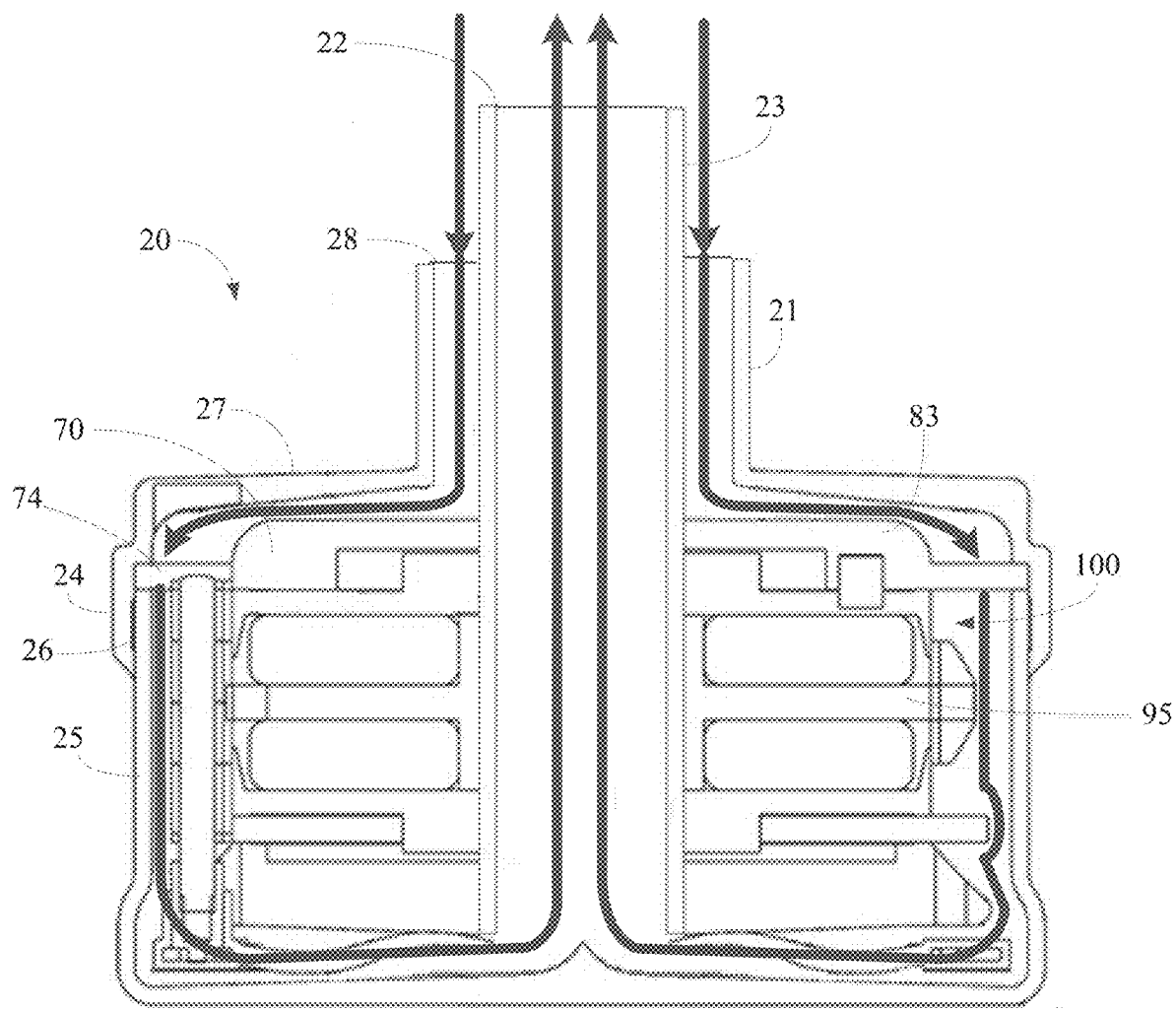
FIG. 6 is a sectional view of the implantable pump of the present invention.

Referring now to FIG. 2, implantable pump 20 in a preferred embodiment consists of upper housing portion 24 joined to lower housing portion 25 along interface 26, for example, by threads or welding, to form fluid tight pump housing 27. Implantable pump 20 includes outflow cannula 23 and inflow cannula 21, as shown in FIG. 1. Outflow cannula 23 and inflow cannula 21 may be rigid, semi-rigid, or non-rigid or may vary in rigidity. Inflow cannula 21 may be integrated or otherwise affixed to upper housing portion 24. Upper housing portion 24 may include an electrical conduit for receiving electrical wires from controller 30 and battery 40. Outflow cannula 23 may be integrated into internal components of implantable pump 20 as illustrated in FIG. 6 and discussed in detail below. Alternatively, outflow cannula 23 may be integrated with or otherwise affixed to upper housing portion 24. In yet another alternative embodiment illustrated in FIG. 7, outflow cannula 23 may be removably coupled to implantable pump 20 at coupling section 52. Inflow cannula 21 and outflow cannula 23 are coaxial with one another and may extend from the center of implantable pump 20 or alternatively may extend from an eccentric position. Inflow cannula 21 is sized and configured to be larger in diameter than outflow cannula 23 such that outflow cannula 23 fits within inflow cannula 21. The annular space between inflow cannula 21 and outflow cannula 23 is sufficient to permit blood to flow between inflow cannula 21 and outflow cannula 23 and preferably extends radially for a distance of at least 0.5 mm. Pump housing 27 is made of a biocompatible material, such as titanium, and is sized to be implanted within a patient's chest.

Referring again to FIG. 1, in one embodiment, controller 30 and battery 40 are extracorporeal, and are sized so as to be placed on a belt or garment worn by the patient. Both controller 30 and battery 40 are electrically coupled to implantable pump 20, for example, via cable 29 that extends through a percutaneous opening in the patient's skin and into an electrical conduit of pump housing 27. Illustratively, battery 40 is electrically coupled to controller 30 via cable 41 that is integrated into belt 42. In an alternative embodiment, controller 30 may be enclosed within a biocompatible housing and sized to be implanted subcutaneously in the patient's abdomen. In this alternative embodiment, controller 30 may include a wireless transceiver for bi-directional communications with an extracorporeal programming device and also include a battery that is continuously and inductively charged via extracorporeal battery 40 and an extracorporeal charging circuit. As will be understood, the foregoing alternative embodiment avoids the use of percutaneous cable 29, and thus eliminates a frequent source of infection for conventional LVAD devices.

Battery 40 preferably comprises a rechargeable battery capable of powering implantable pump 20 and controller 30 for a period time such as several hours, e.g., 8-12 hours, before needing to be recharged. Battery 40 may include a separate charging circuit, not shown, as is conventional for rechargeable batteries. Battery 40 preferably is disposed within a housing suitable for carrying on a belt or holster, so as not to interfere with the patient's daily activities.

Programmer 50 may consist of a conventional laptop computer that is programmed to execute programmed software routines, for use by a clinician or medical professional, for configuring and providing operational parameters to controller 30. The configuration and operational parameter data is stored in a memory associated with controller 30 and used by the controller to control operation of implantable pump 20. As described in further detail below, controller 30 directs implantable pump 20 to operate at specific parameters determined by programmer 50. Programmer 50 preferably is coupled to controller 30 via cable 51 only when the operational parameters of the implantable pump are initially set or periodically adjusted, e.g., when the patient visits the clinician.

In accordance with another aspect of the invention, mobile device 60, which may be a conventional smartphone, may include an application program for bi-directionally and wirelessly communicating with controller 30, e.g., via WiFi or Bluetooth communications. The application program on mobile device 60 may be programmed to permit the patient to send instructions to controller to modify or adjust a limited number of operational parameters of implantable pump 20 stored in controller 30. Alternatively or in addition, mobile device 60 may be programmed to receive from controller 30 and to display on screen 61 of mobile device 60, data relating to operation of implantable pump 20 or alert or status messages generated by controller 30.

Figure 3A:
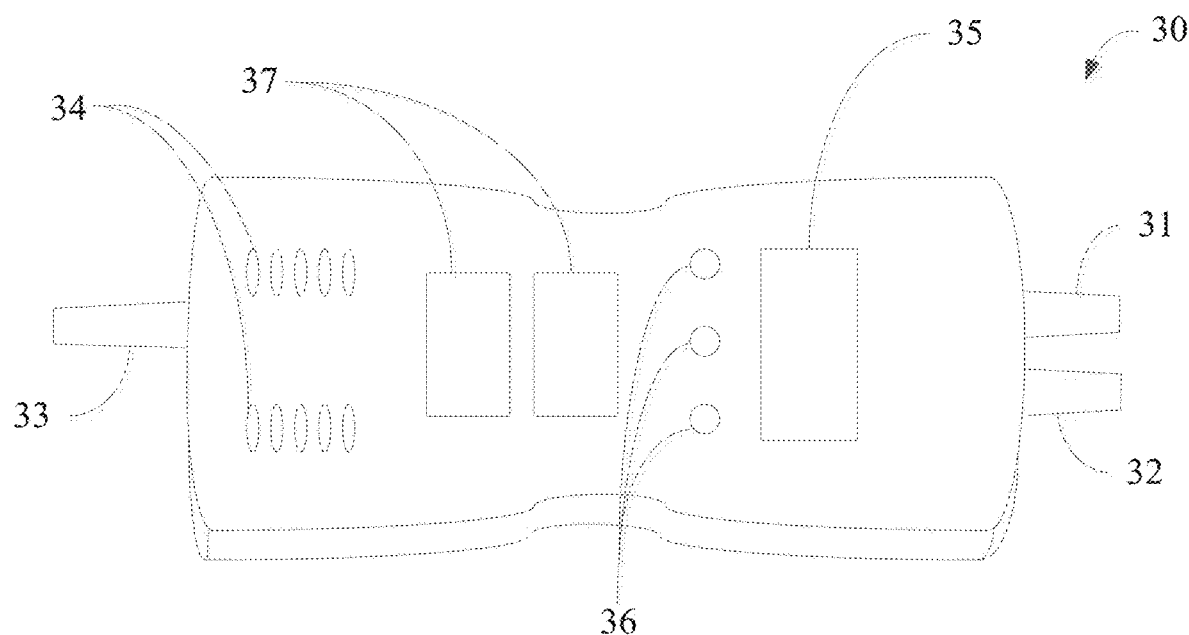
FIGS. 3A and 3B are, respectively, a perspective view and a schematic view of the electronic components of an exemplary embodiment of the controller of the present invention.
Figure 3B:
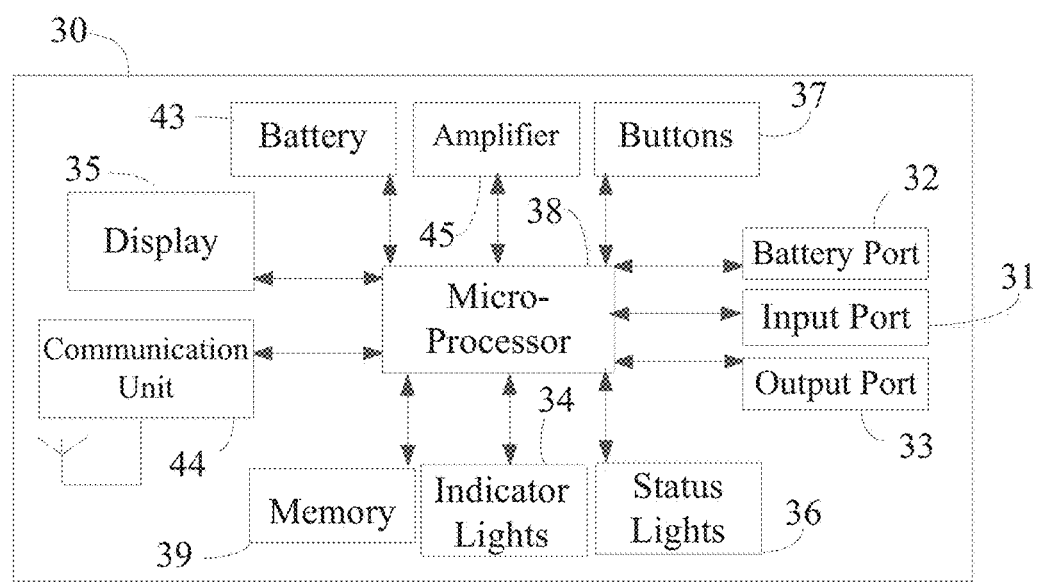

With respect to FIGS. 3A and 3B, controller 30 is described in greater detail. As depicted in FIG. 1, controller 30 may be sized and configured to be worn on the exterior of the patient's body and may be incorporated into a garment such as a belt or a vest. Controller 30 includes input port 31, battery port 32, output port 33, indicator lights 34, display 35, status lights 36 and buttons 37.

Input port 31 is configured to periodically and removably accept cable 51 to establish an electrical connection between programmer 50 and controller 30, e.g., via a USB connection. In this manner, a clinician may couple to controller 30 to set or adjust operational parameters stored in controller 30 for controlling operation of implantable pump 20. In addition, when programmer 50 is coupled to controller 30, the clinician also may download from controller 30 data relating to operation of the implantable pump, such as actuation statistics, for processing and display on display 55 of programmer 50. Alternatively, or in addition, controller 30 may include a wireless transceiver for wirelessly communicating such information with programmer 50. In this alternative embodiment, wireless communications between controller 30 and programmer 50 may be encrypted with an encryption key associated with a unique identification number of the controller, such as a serial number.

Battery port 32 is configured to removably accept cable 41, illustratively shown in FIG. 1 as integrated with belt 42, so that cable 41 routed through the belt and extends around the patient's back until it couples to controller 30. In this manner, battery 40 may be removed from belt 42 and disconnected from controller 30 to enable the patient to periodically replace the battery with a fully charged battery. It is expected that the patient will have available to him or her at least two batteries, so that while one battery is coupled to controller 30 to energize the controller and implantable pump, the other battery may be connected to a recharging station. Alternatively, or in addition, battery port 32 may be configured to accept a cable that is coupled directly to a power supply, such a substantially larger battery/charger combination that permits the patient to remove battery 40 while lying supine in a bed, e.g., to sleep.

Output port 33 is electrically coupled to cable 29, which in turn is coupled to implantable pump 20 through the electrical conduit of pump housing 27. Cable 29 provides both energy to energize implantable pump 20 in accordance with the configuration settings and operational parameters stored in controller 30, and to receive data from sensors disposed in implantable pump 20. In one embodiment, cable 29 may comprise an electrical cable having a biocompatible coating and is designed to extend percutaneously. Cable 29 may be impregnated with pharmaceuticals to reduce the risk of infection, the transmission of potentially hazardous substances or to promote healing where it extends through the patient's skin.

As mentioned above, controller 30 may include indicator lights 34, display 35, status lights 36 and buttons 37. Indicator lights 34 may visually display information relevant to operation of the system, such as the remaining life of battery 40. Display 35 may be a digital liquid crystal display that displays real time pump performance data, physiological data of the patient, such as heart rate, or operational parameters of the implantable pump, such as the target pump pressure or flow rate, etc. When it is determined that certain parameter conditions exceed preprogrammed thresholds, an alarm may be sounded and an alert may be displayed on display 35. Status lights 36 may comprise light emitting diodes (LEDs) that are turned on or off to indicate whether certain functionality of the controller or implantable pump is active. Buttons 37 may be used to wake up display 35, to set or quiet alarms, etc.

With respect to FIG. 3B, the components of the illustrative embodiment of controller 30 of FIG. 3A are described. In addition to the components of controller 30 described in connection with FIG. 3A, controller 30 further includes microprocessor 38, memory 39, battery 43, optional transceiver 44 and amplifier 45. Microprocessor may be a general purpose microprocessor, for which programming to control operation of implantable pump 20 is stored in memory 39. Memory 39 also may store configuration settings and operational parameters for implantable pump 20. Battery 40 supplies power to controller 30 to provide continuity of operation when battery 40 is periodically swapped out. Optional transceiver 44 to facilitates wireless communication with programmer 50 and/or mobile device 60 via any of a number of well-known communications standards, including BLUETOOTH™, ZigBee, and/or any IEEE 802.11 wireless standard such as Wi-Fi or Wi-Fi Direct. Controller 30 further may include amplifier circuitry for amplifying electrical signals transferred between controller 30 and implantable pump 20.

Figure 4:
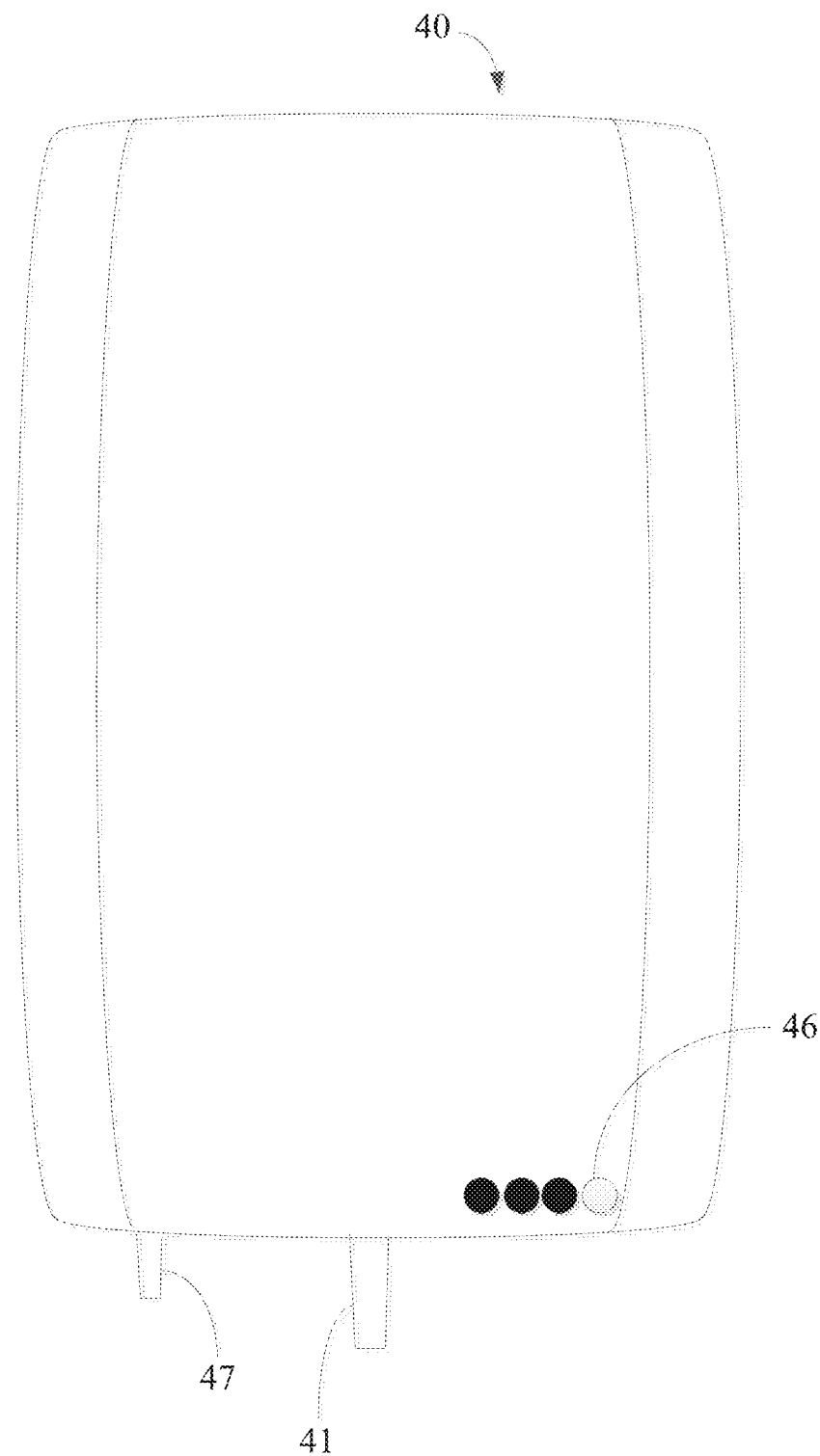
FIG. 4 is a plan view of an extracorporeal battery for use in the pump system of the present invention.

Referring now to FIG. 4, battery 40 is described. Battery 40 provides power to implantable pump 20 and also may provide power to controller 30. Battery 40 may consist of a single battery or a plurality of batteries disposed within a housing, and preferably is sized and configured to be worn on the exterior of the patient's body, such as on belt 42. Battery life indicator 46 may be provided on the exterior of battery 40 to indicate the degree to the remaining charge of the battery. Cable 41 may have one end removably coupled to battery 40 and the other end removably coupled to battery port of controller 30 to supply power to energize implantable pump 20. In one embodiment, battery 40 may be rechargeable using a separate charging station, as is known in the art of rechargeable batteries. Alternatively, or in addition, battery 40 may include port 47 which may be removably coupled to a transformer and cable to permit the battery to be recharged using a conventional residential power outlet, e.g., 120 V, 60 Hz AC power.

Figure 5A:
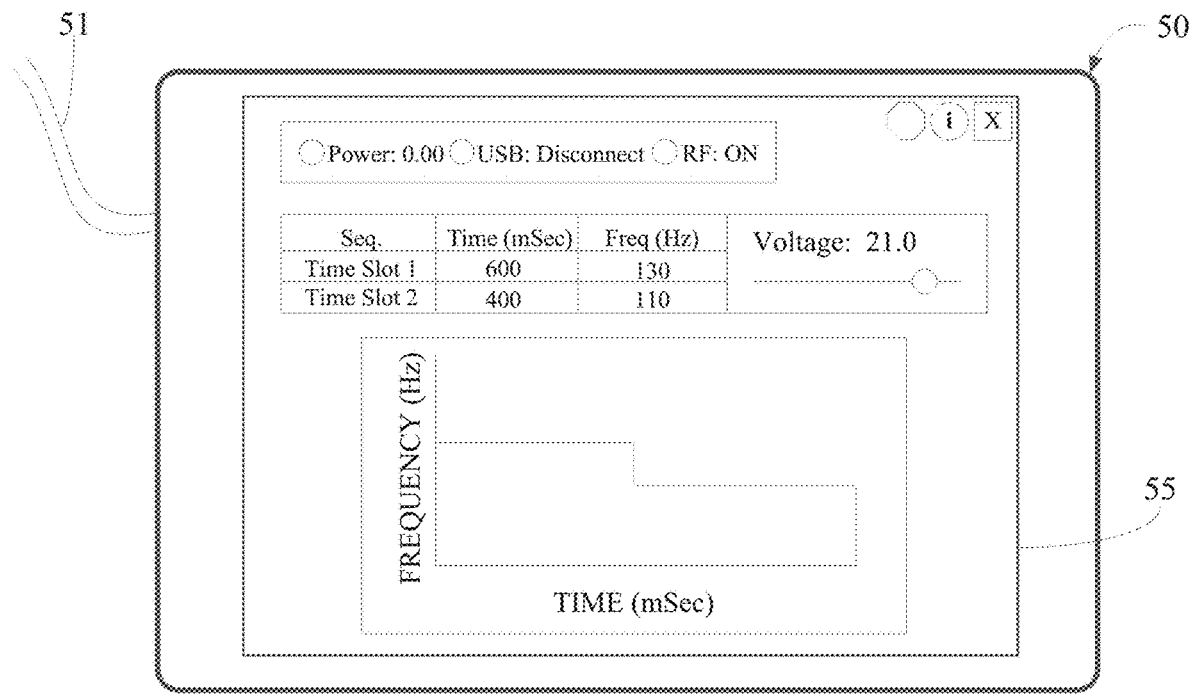
FIGS. 5A and 5B are, respectively, a perspective view and a schematic view of the electronic components of an exemplary embodiment of the programmer of the present invention.
Figure 5B:
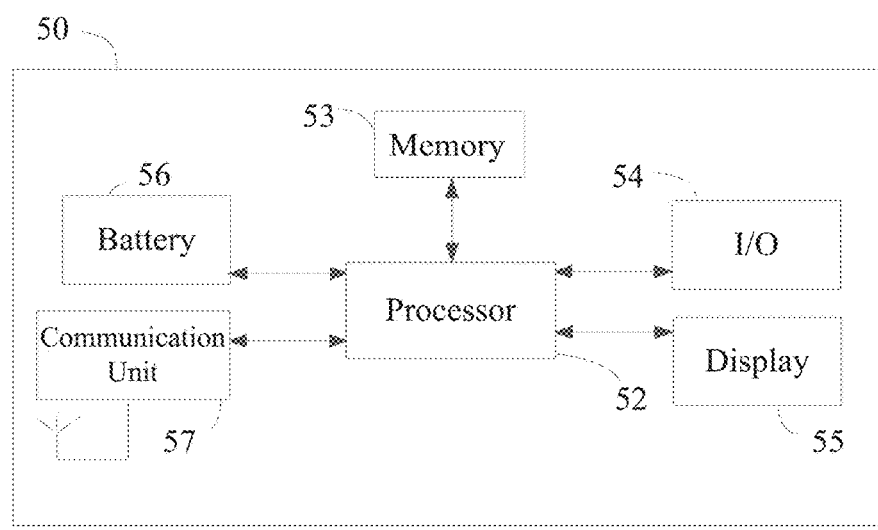

Referring now to FIGS. 5A-5B, programmer 50 is described. Programmer 50 may be a conventional laptop loaded with programmed software routines for configuring controller 30 and setting operational parameters that controller 30 uses to control operation of implantable pump 20. As discussed above, programmer 50 typically is located in a clinician's office or hospital, and is coupled to controller 30 via cable 51 or wirelessly to initially set up controller 30, and then periodically thereafter as required to adjust the operational parameters as may be needed. The operation parameters of controller 30 set using the programmed routines of programmer 50 may include but are not limited to applied voltage, pump frequency, pump amplitude, target flow rate, pulsatility, etc. When first implanted, the surgeon or clinician may use programmer 50 to communicate initial operating parameters to controller 30. Following implantation, the patient periodically may return to the clinician's office for adjustments to the operational parameters which may again be made using programmer 50.

Programmer 50 may be any type of conventional personal computer device such as a laptop or a tablet computer having touch screen capability. As illustrated in FIG. 5B, programmer 50 preferably includes processor 58, memory 53, input/output device 54, display 55, battery 56 and communication unit 57. Memory 53 may include the operating system for the programmer, as well as the programmed routines needed to communicate with controller 30. Communication unit 57 may include any of a number of well-known communication protocols, such as BLUETOOTH™, ZigBee, and/or any IEEE 802.11 wireless standard such as Wi-Fi or Wi-Fi Direct. As illustrated in FIG. 5A, the programmed routines used to program and communicate with controller 30 also may provide data for display on the screen of programmer 50 identifying operational parameters with which controller 30 controls implantable pump 20. The programmed routines also may enable programmer 50 to download from controller 30 operational data or physiologic data communicated by the implantable pump and to display that information in real time while the programmer is coupled to the controller via a wired or wireless connection. The transferred data may then be processed and displayed on the screen of programmer 50.

Referring to FIG. 6, a sectional view of implantable pump 20 is shown. The pump illustrated in FIG. 6 is a vibrating membrane pump. However, it is understood that implantable pump 20 may employ any type of pump well-suited for use as a left ventricular assist device and sized and configured to fit within pump housing 27. As is illustrated in FIG. 6, pump housing 27 includes upper housing portion 24 joined to lower housing portion 25 along interface 26. As also illustrated in FIG. 6, pump housing and the pump are configured to orient inflow cannula 21 and outflow cannula 23 in a coaxial orientation. Inflow cannula 21 may be separate and distinct from upper housing portion 24 or may alternatively be incorporated into the same component, as is shown in FIG. 6. Outflow cannula 23 may be incorporated into pump assembly 70, as is shown in FIG. 6. For example, outflow cannula may be affixed to or may extend from a stator of a vibrating membrane pump. Alternatively, outflow cannula 23 may be coupled to inflow cannula 21 or to upper housing portion 24 in a manner that permits blood to flow between inflow cannula 21 and outflow cannula 23. For example, inflow cannula 21 may suspend outflow cannula 23 in a coaxial manner using struts that extend out from inflow cannula 21 and permit blood to flow between inflow cannula 21 and outflow cannula 23.

Inflow cannula 21 and outflow cannula 23 are configured to be in fluid communication with one another such that blood enters an inlet 28 of inflow cannula 21, travels through annular inflow cannula 21 and fills up the pump. The pump increases flow and pressure and directs blood from the pump into outflow cannula 23 and ultimately out outlet 22. In this manner, blood may enter and exit from the same general area such as the same heart chamber. As outflow cannula 23 is configured to extend beyond inflow cannula 21, the blood that exits outflow cannula 23 is not likely to enter inflow cannula 21.

Figure 7:
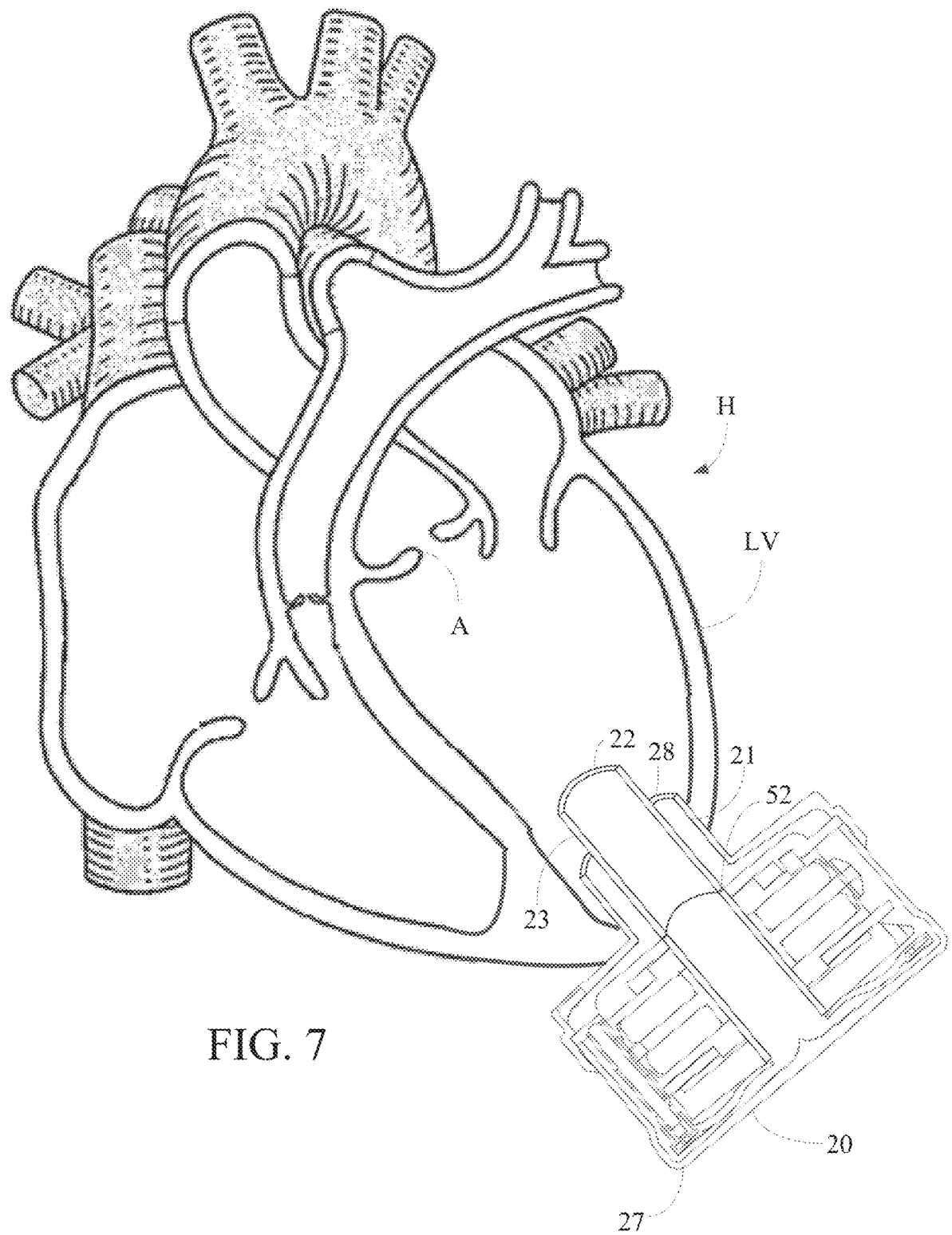
FIG. 7 is a sectional view the implantable pump of the present invention implanted into the left ventricle.

Referring now to FIG. 7, implantable pump 20 is shown implanted into the left ventricle of a heart. The pump illustrated in FIG. 7 is a vibrating membrane pump. However, it is understood that implantable pump 20 may employ any type of pump well-suited for use as a left ventricular assist device and sized and configured to fit within pump housing 27. As is described above, implantable pump 20 is configured to be implanted within a patient's chest through a thoracotomy. Implantable pump 20 may be affixed to the exterior of the patient's heart using a ring-suture or other conventional technique. Outflow cannula 23 and inflow cannula 21 are configured to extend through the wall of the left ventricle and extend into the left ventricle as is shown in FIG. 7. FIG. 7 illustrates an embodiment of implantable pump 20 where outflow cannula 23 may be removably attached to implantable pump 20 at coupling section 52. Outflow cannula 23 may be coupled to implantable pump 20 at coupling section 52 using well-known methods. For example, outflow cannula 23 may be threaded and coupling section 52 may be configured to receive the threads of outflow cannula 23 resulting in a fluid-tight seal. However, it is understood that other conventional methods for removably coupling implantable pump 20 to outflow cannula 23 may be used. Implantable pump 20 may be affixed to the apex of the left ventricle to position the inflow catheter near the bottom of the left ventricle, wherein blood typically accumulates, to maximize the blood available for pumping.

With both inlet 28 of inflow cannula 21 and outlet 22 of outflow cannula 23 located in the left ventricle, the need for an outflow cannula or other hose-like structure that extends outside the heart and connects to the aorta via aortic anastomosis is eliminated. Blood can be directed out of outflow cannula 23 either into or towards the aorta from within the heart. Without the need for a long hose-type structure, blood can more efficiently travel from the pump to the aorta. Further, the risk of backflow into the pump is significantly reduced as the aortic valve naturally prevents backflow during diastole. As such, the pump is not required to run at a low flow state to prevent backflow, a technique that increases the risk of damaging the blood.

Figure 8:
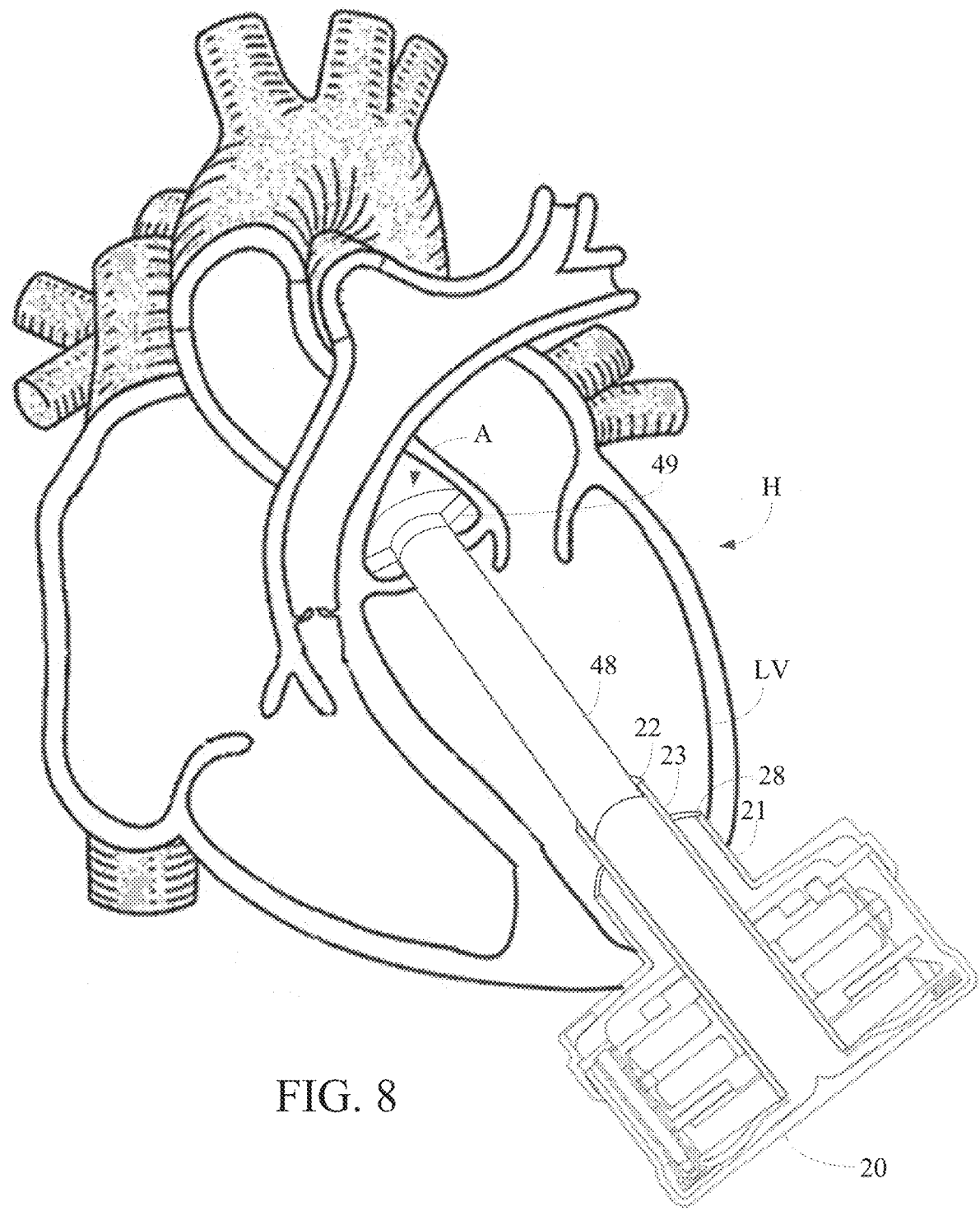
FIG. 8 is a sectional view the implantable pump of the present invention implanted into the left ventricle having an outflow conduit extending into the aorta.

One way of delivering oxygen-rich blood to the aorta is by employing outflow conduit 48 as shown in FIG. 8. Outflow conduit 48 is a tubular, hose-type structure and may be flexible, semi-rigid or rigid, or may vary in rigidity throughout outflow conduit 48. Outflow conduit 48 has a first and second end. In FIG. 8, the same implantable pump of FIG. 7 is illustrated affixed to the left ventricle. Like in FIG. 7, outflow cannula 23 and inflow cannula 21 both extend into the left ventricle such that outlet 22 and inlet 28 exist within the left ventricle. As shown in FIG. 8, outflow conduit 48 may be coupled to outlet 22 of outflow cannula 23 at the first end. Outflow conduit 48 may be sized to fit within outflow cannula or alternatively to fit over outflow cannula 23 and make a fluid tight seal with outflow cannula 23. The second end of outflow conduit 48 is configured to traverse the aortic valve and extend past the aortic valve. Outflow conduit 48 may be coupled at the one end to positioning device 49 which may be compressible and may be configured to expand to engage a wall of aorta A. For example, positioning device 49 may be an expandable stent. In this configuration, positioning device 49 may position outflow conduit 48 in the center of the aortic valve as positioning device expands to engage a wall of aorta A.

In another embodiment, outflow conduit 48 may be configured at the first end to be removably coupled with implantable pump 20 at coupling section 52. Outflow conduit 48 may be coupled to implantable pump 20 at coupling section 52 using various well-known coupling techniques resulting in a fluid tight seal. For example, outflow conduit 48 may include threads at the first end and coupling section 52 may be configured to receive the threads of outflow conduit 48. However, it is understood that implantable pump 20 may be removably coupled to outflow conduit 48 using other conventional techniques. In this alternative embodiment, outflow cannula 23 would not be needed.

The second end of outflow conduit 48 may be sized to permit the aortic valve to open and close naturally around outflow conduit 48. In this manner, when the aortic valve is open, blood may enter the aorta from the left ventricle by flowing between the aortic valve and an outer surface of outflow conduit 48. When the aortic valve is closed, the aortic valve may create a seal around outflow conduit 48 to prevent blood from flowing between outflow conduit 48 and the aortic valve. Alternatively, outflow conduit 48 may be sized to fit through the aortic valve in such a manner that no blood is permitted to flow between the aortic valve and an outer surface of outflow conduit 48 at any time.

With outflow conduit 48 coupled to outflow cannula 23 and extending into and through the aortic valve, and inflow cannula extending into the left ventricle near the apex of the left ventricle, blood is permitted to enter inflow cannula 21, flow through inflow cannula 21 and enter the pump. The pump generates flow and pressure and directs the blood from the pump to outflow cannula 23 and from outflow cannula 23 to outflow conduit 48. From outflow conduit 48 blood is propelled through the aortic valve and into the aorta.

Figure 9:
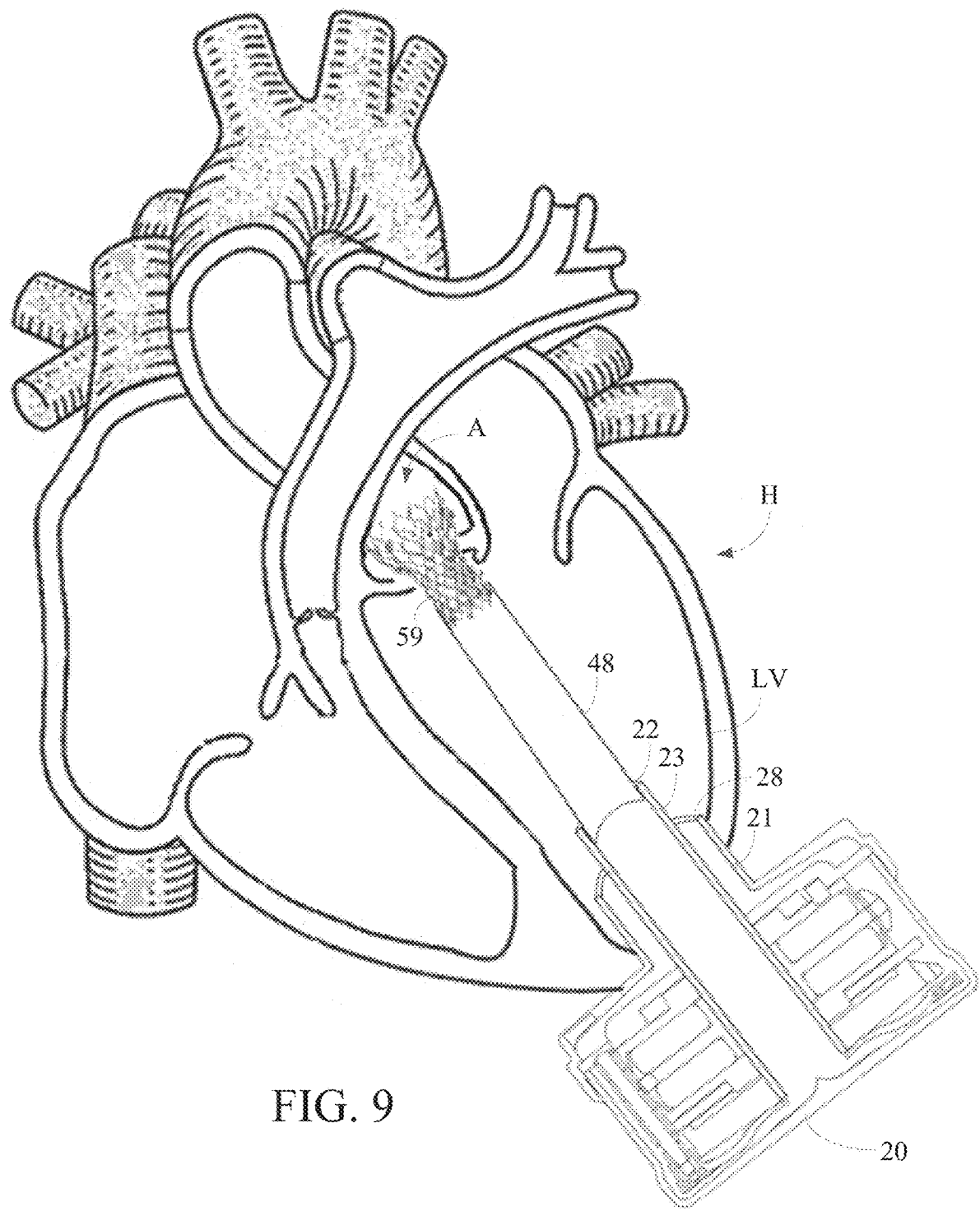
FIG. 9 is a sectional view the implantable pump of the present invention implanted into the left ventricle having an outflow conduit affixed to a stent mounted valve.

Referring now to FIG. 9, implantable pump 20 is shown implanted at the same location as FIGS. 7 and 8. Also, like FIG. 8, outflow cannula 23 of implantable pump 20 is coupled to a first end of outflow conduit 48 at outlet 22. At a distal end of outflow conduit 48, outflow conduit 48 may be coupled to stent mounted valve 59 which may be expandable. Stent mounted valve 59 may be any type of valve mounted upon a stent and that may be positioned within the aortic valve. Stent mounted valve 59 is designed to only permit flow in one direction.

Like the connection between the first end of outflow conduit 48 and outflow cannula 23, the connection between the second end of outflow conduit 48 and stent mounted valve 59 may be a conventional fluid tight seal. In one embodiment, stent mounted valve 59 may be any type of well-known transcatheter aortic valve device capable of being coupled to the tubular outflow conduit such as a transcatheter aortic valve replacement (TAVR). A TAVR may include a valve portion and a mesh structure having an anchoring portion. A TAVR may repair the aortic valve without removing the native valve or alternatively may replace a surgically removed valve. Use of a TAVR as stent mounted valve 59 may be appropriate where the aortic valve has been damaged, is diseased or has otherwise been compromised.

In the configuration shown in FIG. 9, stent mounted valve 59 is anchored to the wall of the aorta and/or aortic valve, thereby securing outflow conduit 48 to the aortic valve. As the blood flow to the aorta is marshalled by stent mounted valve 59, blood flow into the aortic valve is permitted but backflow from the aorta to implantable pump 20 is prevented by stent mounted valve 59. In this manner, blood flows from the left ventricle into implantable pump 20 and from implantable pump 20 blood is guided directly to the aorta through stent mounted valve 59 and prevented from reentering outflow conduit 48 by stent mounted valve 59.

Stent mounted valve 59 may be introduced to the aortic valve in a number of different ways. For example, stent mounted valve 59 may be introduced by a transcatheter method. Alternatively, stent mounted valve 59 may be introduced over a medical component other than a catheter, may be introduced transapically, or even through the pump. Where stent mounted valve 59 is introduced through the pump, the procedure may involve coring the left ventricle apex, introducing implantable pump 20 at the apex, inserting a valve placement component through an opening in the base of the pump as is discussed in greater detail below, deploying stent mounted valve 59 over or with the aid of the valve placement component, connecting stent mounted valve 59 to outflow conduit 48, and removing the valve placement component.

Figure 10:
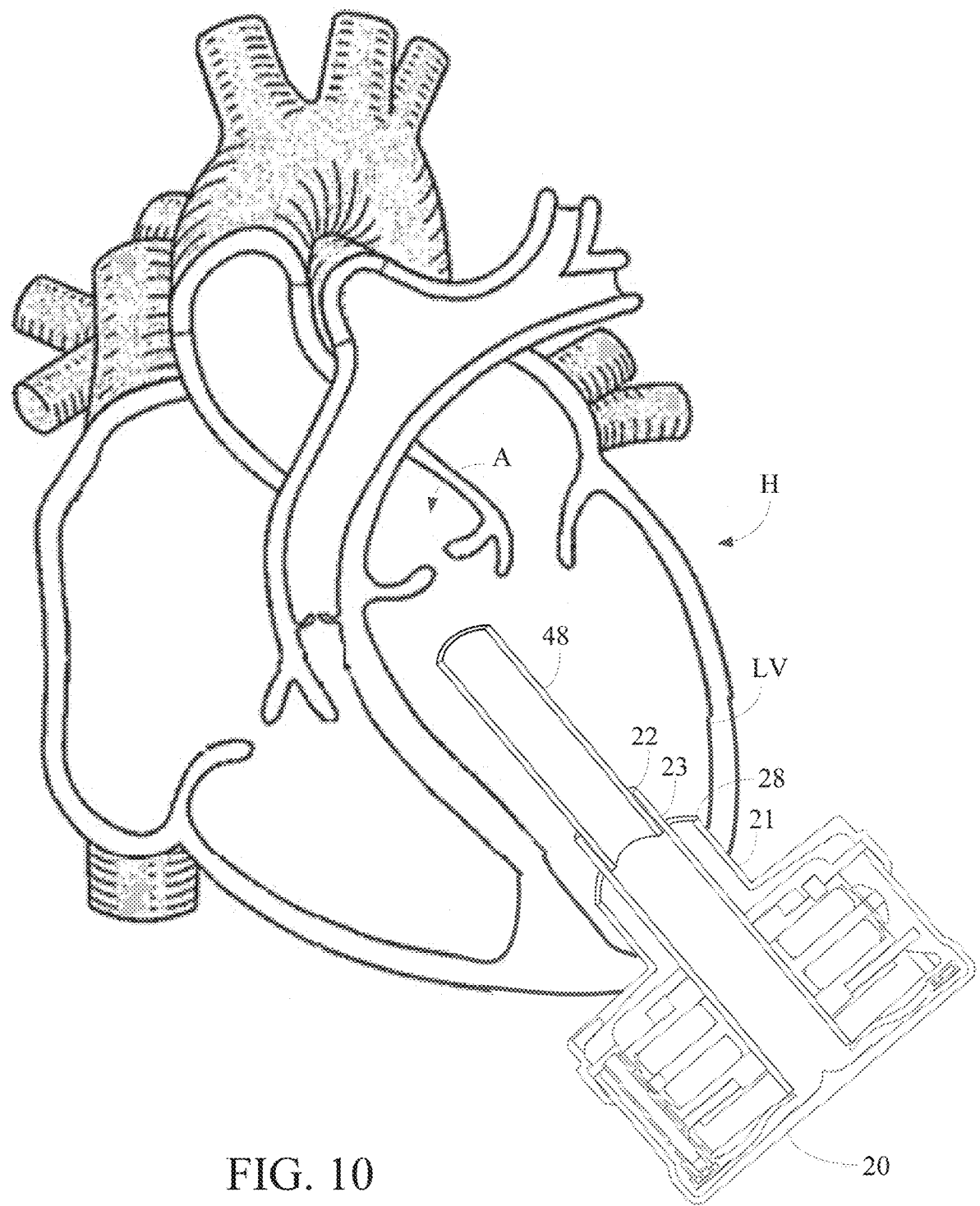
FIG. 10 is a sectional view of the implantable pump of the present invention implanted into the left ventricle having an outflow conduit suspended within the left ventricle.

Referring now to FIG. 10, implantable pump 20 is shown implanted at the same location as FIG. 9. Like in FIG. 9, inflow cannula 21 and outflow cannula 23 both extend into the left ventricle near the apex of the left ventricle. The pump in FIG. 10, like the pump in FIGS. 8 and 9, is similarly coupled to outflow conduit 48. Outflow conduit 48 is coupled to outlet 22 of outflow cannula 23 at a first end and is freestanding at a second end. The freestanding second end of outflow conduit 48 extends towards the aortic valve. The freestanding second end of outflow conduit 48 does not extend all the way to the aortic valve but terminates at or prior to reaching the aortic valve annulus. Outflow conduit 48 may be semi-rigid or rigid throughout or along a portion of outflow conduit to maintain an orientation toward the aortic valve. Implantable pump 20, arranged in this configuration, is configured to accept blood from inflow cannula 21, pump blood to outflow cannula 23 and direct blood toward the aortic valve through outflow conduit 48. The momentum of the blood flow propelled out of outflow conduit 48 toward the aortic valve is intended to carry the blood through the aortic valve. As outflow conduit 48 does not directly interact with the aortic valve, blood is free to enter the aortic valve directly from the left ventricle.

Figure 11:
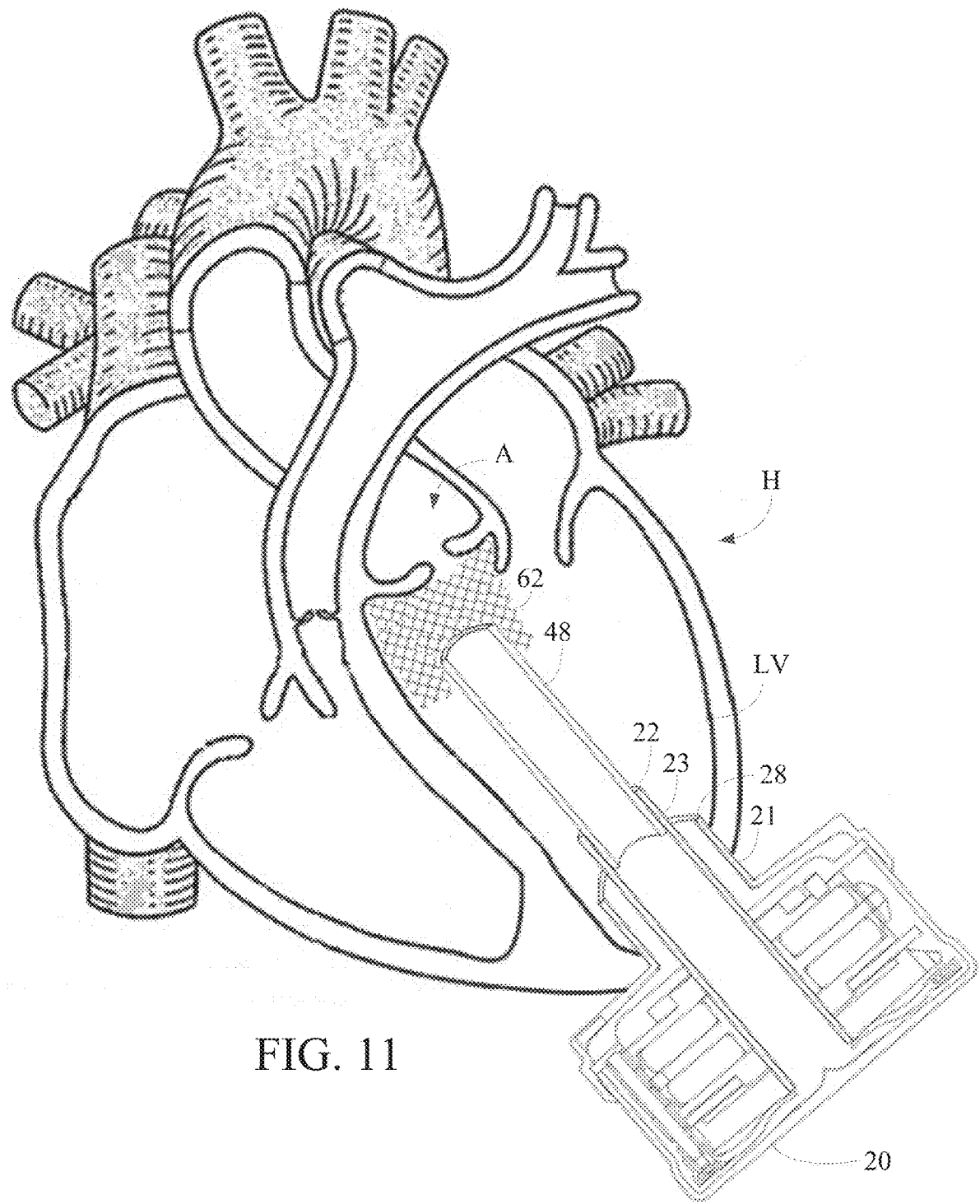
FIG. 11 is a sectional view of the implantable pump of the present invention implanted into the left ventricle having an outflow conduit anchored to the left ventricular outflow tract.

Referring now to FIG. 11, implantable pump 20 is illustrated in nearly the same configuration as is shown in FIG. 10 such that both inflow cannula 21 and outflow cannula 23 extend into the left ventricle and outflow conduit 48 extends out from outflow cannula 23. Like the pump configuration shown in FIG. 10, outflow conduit 48 is coupled to outflow cannula 23 at a first end and extends toward the aortic valve at a second end but does not reach the aortic valve. Unlike the freestanding outflow conduit illustrated in FIG. 10, outflow conduit 48 in FIG. 11 is not freestanding but is instead secured in a position directed towards the aortic valve. Also unlike the outflow conduit illustrated in FIG. 10, outflow conduit 48 in FIG. 11 may be flexible, semi-rigid or rigid. Anchor 62 is shown in FIG. 11 coupled to outflow conduit 48 and also affixed to at least the ventricular outflow tract below the aortic valve such that outflow conduit 48 is secured in a positioned oriented toward the aortic valve. Anchor 62 may alternatively be affixed only to an inner wall of the left ventricle or both an inner wall of the left ventricle and the ventricular outflow tract. Anchor 62 may be a biocompatible mesh such as a plastic or synthetic mesh configured to be affixed to both cardiac tissue and the second end of outflow conduit 48. As was the case for the pump in FIG. 10, blood is free to enter the aortic valve directly from the left ventricle.

Figure 12:
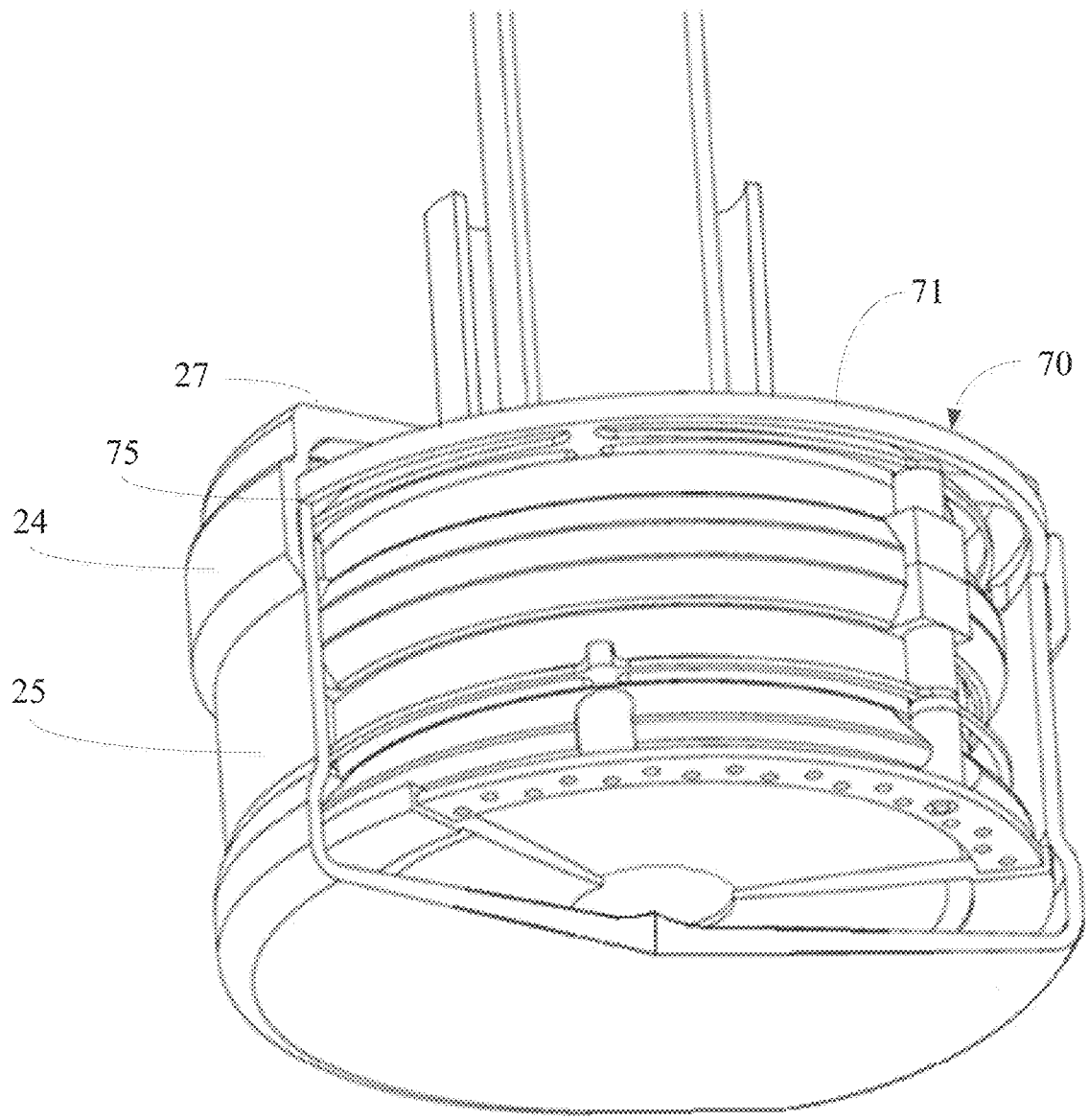
FIG. 12 is a perspective cut-away view of the pump assembly of the implantable pump of the present invention.

As illustrated in FIGS. 6-11, implantable pump 20 may be a vibrating membrane pump. An exemplary vibrating membrane pump is shown in FIGS. 12-19. Referring now to FIG. 12, pump assembly 70 is configured to fit within pump housing 27. Pump assembly 70 is secured to pump housing 27 by fixation ring 71. Fixation ring 71 extends out from and around pump assembly 70 and may be secured between upper housing portion 24 and lower housing portion 25 when the housing portions are assembled. In this manner, pump assembly 70 is disposed in pump housing 27 such that fixation ring 71 is captured and secured on step 75 formed between upper housing portion 24 and lower housing portion 25. Pump assembly 70 is prevented from moving within pump housing 27. Pump housing 27 preferably is sized and configured to conform to pump assembly 70 such that pump assembly 70 does not contact the interior of the pump housing at any location other than at fixation ring 71.

While lower housing portion 25 is illustrated in FIG. 12 as having a smooth bottom surface that extends the entire diameter of lower housing portion 25, lower housing portion 25 alternatively may have an open section offering access to pump assembly 70 and/or outflow cannula 23. Lower housing portion 25 may have a removable bottom portion revealing an opening nearly the entire diameter of lower housing portion 25. Alternatively, or in addition, lower housing portion 25 may have a smaller diameter opening that may be closed using a plug.

Figure 13A:
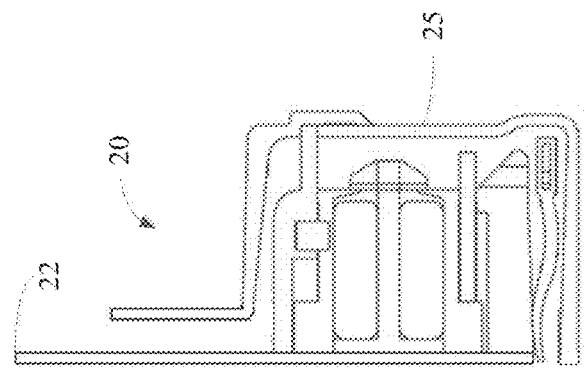
FIGS. 13A, 13B, and 13C are a sectional views of the implantable pump of the present invention with a plug.
Figure 13A:
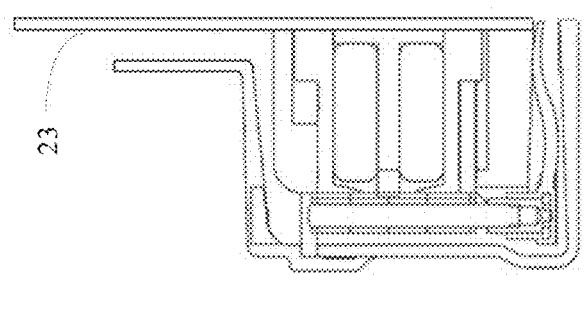
Figure 13B:
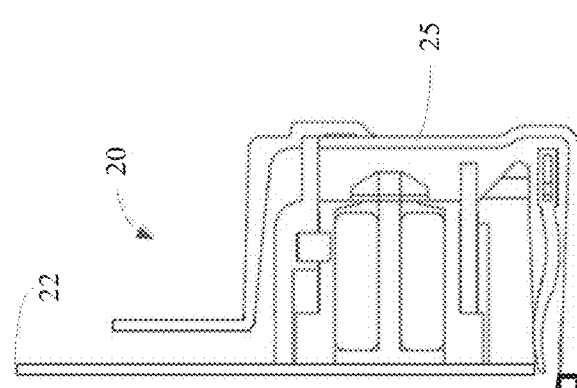
Figure 13B:

Referring now to FIG. 13A, lower housing portion 25 is illustrated having plug 63, providing access to pump assembly 70 and outflow cannula 23. Plug 63 may be a removable portion of lower housing portion 25 and may be located in the center of the bottom surface of lower housing portion 25 to provide access to outflow cannula 23. As such, removal of plug 63 may permit access to outlet 22 of outflow cannula 23 via the bottom of implantable pump 20. Plug 63 may be threaded and lower housing portion 25 may be configured to receive threaded plug 63. In this manner, plug 63 may be unscrewed to be removed as is illustrated in FIG. 13B. Alternatively, plug 63 may be sized and configured to fit snugly within lower housing portion 25 and/or may lock into place using any well-known locking mechanism.

Referring now to FIG. 13B, removing plug 63 to provide access to outflow cannula 23 may facilitate minimally invasive procedures or approaches involving implantable pump 20, such as placing the pump in the patient. For example, the pump may be introduced and placed using ventricular coring, occluding with a balloon and introducing the pump over the balloon at which point plug 63 may be closed or otherwise coupled to lower housing portion 25.

Figure 13C:
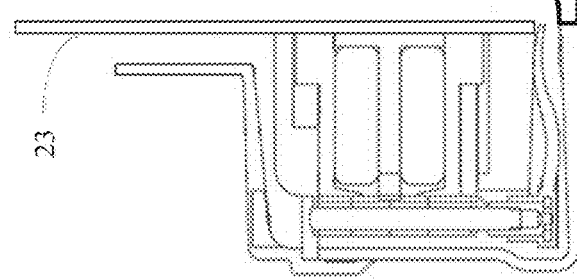
Figure 13C:
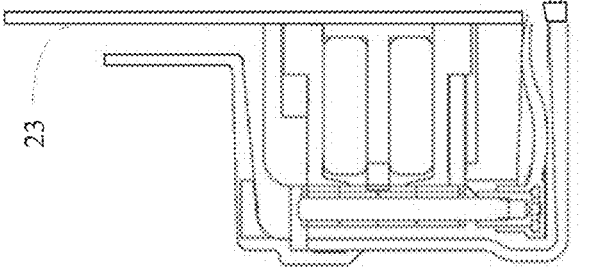

As is illustrated in FIG. 13C, valve plug 64 alternatively may be incorporated in lower housing portion 25. Valve plug 64 may be coupled to lower housing portion 25 in the same manner as described above with regarding to plug 63. Unlike plug 63, valve plug 64 may have a valve portion through which instruments, tools, fluids and other medical components may be introduced. Valve plug 64, having a valve portion, may seal around the various instruments going through the valve portion, thereby permitting instruments access to pump assembly 70 and/or outflow cannula 23, while at the same time preventing other fluids and things from traversing the valve and accessing pump assembly 70 and/or outflow cannula 23.

Figure 14:
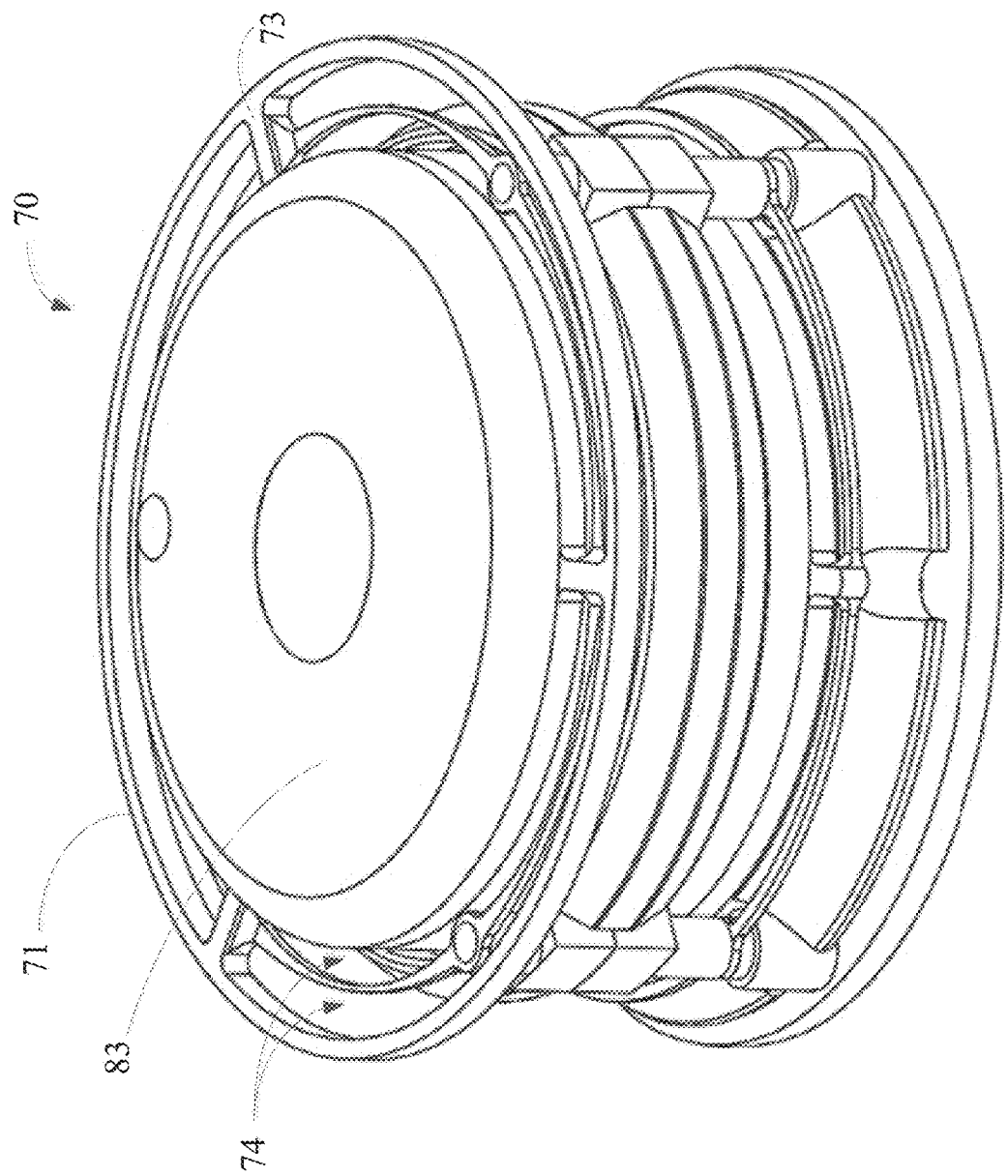
FIG. 14 is a perspective view of the pump assembly of the implantable pump of the present invention.

Referring now to FIG. 14, pump assembly 70 is illustrated in more detail. As is shown in FIG. 14, fixation ring 71 may be a rigid annular structure that is disposed concentrically around tapered section 83, having a larger diameter than tapered section 83. Tapered section 83 does not move relative to fixation ring 71 or pump housing 27. Fixation ring 71 may be rigidly coupled to tapered section 83 via struts 73. Struts 73 create gap 74 between fixation ring 71 and tapered section 83, which preferably is 0.5 mm at its most restricted point.

Figure 15:
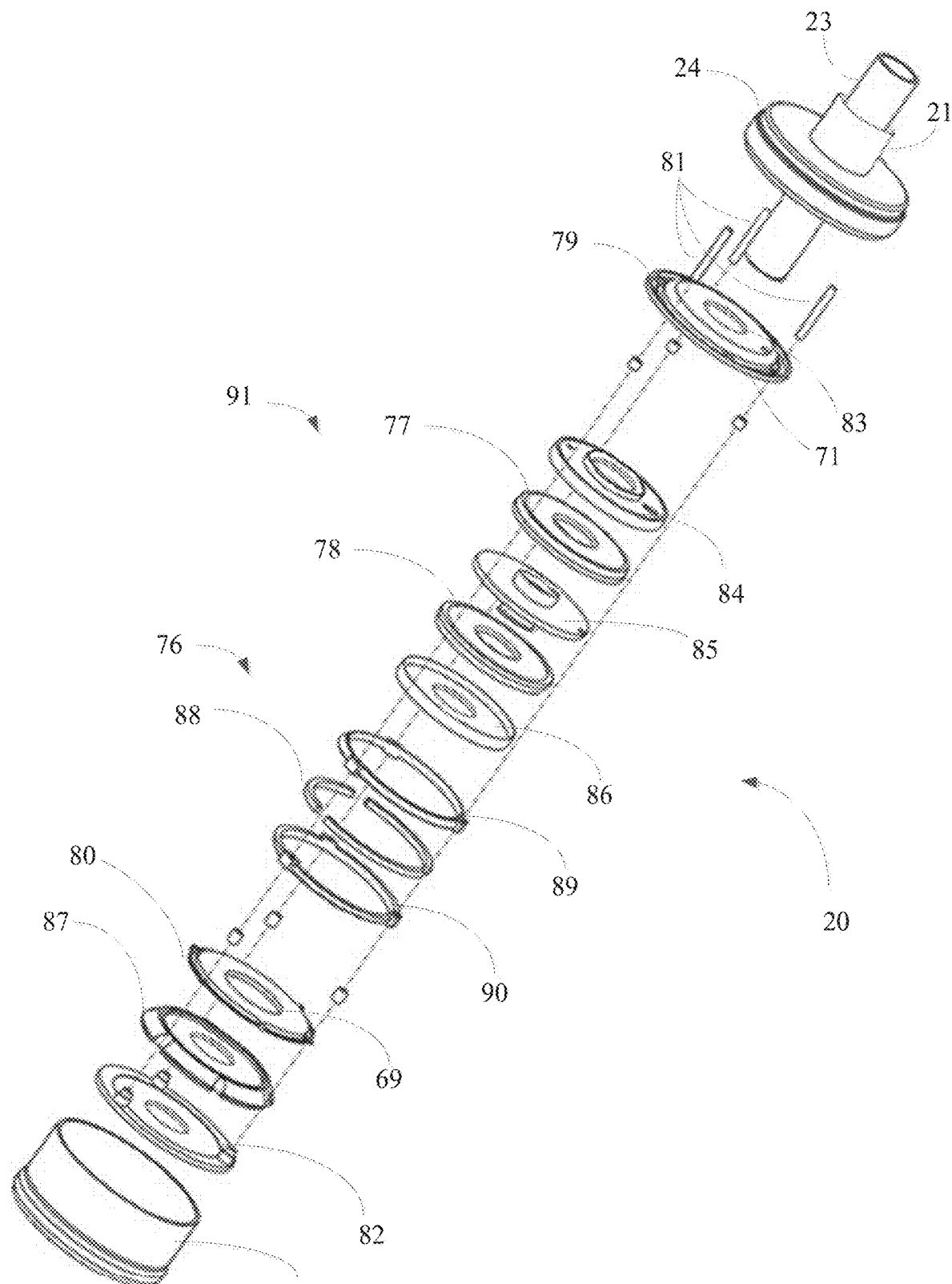
FIG. 15 is an exploded view of the implantable pump of the present invention.
Figure 16:
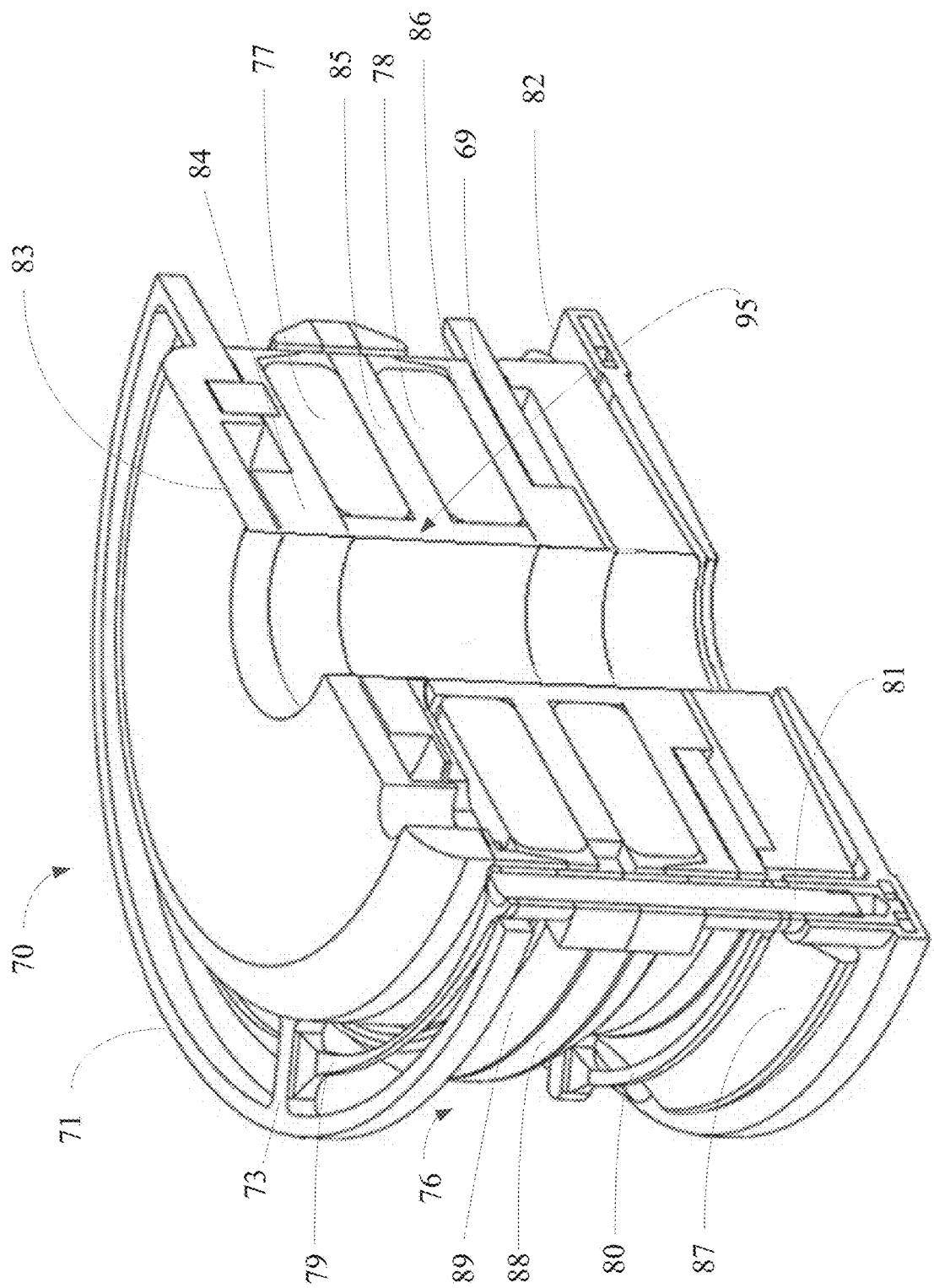
FIG. 16 is a perspective cross sectional view of the pump assembly of the present invention.

FIG. 15 is an exploded view of implantable pump 20. FIG. 16 is a perspective sectional view of pump assembly 70. FIGS. 15 and 16 depict the arrangement of the internal components of pump assembly 70. In particular, pump assembly 70 comprises stator assembly 72, electromagnet assembly 91, magnetic ring assembly 76, fixation ring 71, first suspension ring 79, second suspension ring 80, posts 81 and membrane assembly 82. Stator assembly 72 comprises tapered section 83, flanged portion 87 and suspension ring platform 69 which connects tapered section 83 to flanged portion 87. Magnetic ring assembly 76 comprises magnet ring 88 and magnet ring holder portions 89 and 90. First and second electromagnetic coils 77 and 78, together with electromagnetic holder portions 84, 85 and 86 form electromagnet assembly 91. Electromagnet assembly 91 together with stator assembly 72 form actuator assembly 95. Actuator assembly 95 together with magnetic ring assembly 76 in turn forms the actuator system of implantable pump 20.

First electromagnetic coil 77 and second electromagnetic coil 78 are concentrically sandwiched between electromagnetic holder portions 84, 85 and 86 to form electromagnet assembly 91. Tapered section 83, which is coupled to fixation ring 71 and first suspension spring 79, is located concentrically atop electromagnet assembly 91. Magnet ring 88 is disposed within magnet ring holder portions 89 and 90 to form magnetic ring assembly 76, which is concentrically disposed for reciprocation over electromagnet assembly 91. Suspension ring platform 69 is concentrically disposed between flanged portion 87 and electromagnet assembly 91. Second suspension spring 80 is suspended from suspension ring platform 69. Posts 81 engage first suspension ring 79, magnetic ring assembly 76 and second suspension ring 80 at equally spaced locations around the actuator assembly. Membrane assembly 82 is positioned concentrically below flanged portion 87 and engaged with posts 81.

During use of implantable pump 20, actuator assembly 95 remains stationary relative to pump housing 27. First electromagnetic coil 77 and second electromagnetic coil 78 are separated by electromagnetic holder portion 85. Controller 30 and battery 40 are electrically coupled to electromagnetic coils 77 and 78 to supply current to electromagnetic coils 77 and 78. First electromagnetic coil 77 and second electromagnetic coil 78 may be in electrical communication with one another or may be configured to operate independently and have separate wired connections to controller 30 and battery 40. Electromagnetic coils 77 and 78 may be made of any electrically conductive metallic material such as copper and further may comprise of one or more smaller metallic wires wound into a coil. The wires of the electromagnetic coils are insulated to prevent shorting to adjacent conductive material.

Actuator assembly 95 is surrounded by first suspension ring 79 and second suspension ring 80. Suspension rings 79 and 80 are annular in shape and fit concentrically around actuator assembly 95. First suspension ring 79 preferably is rigidly affixed to tapered section 83 via struts 73 extending from the suspension ring to the stator assembly. As discussed above, struts 73 also affix fixation ring 71 to stator assembly 72. Fixation ring 71 and first suspension spring 79 may be sized and positioned such that a gap of no less than 0.5 mm exists between first suspension ring 79 and fixation ring 71. Second suspension ring 80 similarly is rigidly affixed via struts to suspension ring platform 69. Suspension rings 79 and 80 preferably are sized and shaped such that when suspension rings 79 and 80 are positioned surrounding actuator assembly 95, a gap of no less than 0.5 mm exists between actuator assembly 95 and suspension rings 79 and 80.

First suspension ring 79 and second suspension ring 80 may comprise titanium or stainless steel having elastic properties and which exhibits a spring force when deflected in a direction normal to the plane of the spring. First suspension ring 79 and second suspension ring 80 are substantially rigid with respect to forces applied tangential to the suspension ring. In this manner, first suspension ring 79 and second suspension ring 80 exhibit a spring tension when deformed up and down relative to a vertical axis of the actuator assembly but rigidly resist movement along any other axis, e.g., tilt or twist movements.

Magnetic ring assembly 76 is annular in shape and concentrically surrounds actuator assembly 95. Magnet ring 88 may comprise one or more materials exhibiting magnetic properties such as iron, nickel, cobalt or various alloys. Magnet ring 88 may be made of a single unitary component or comprise several magnetic components that are coupled together. For example, magnet ring 88 may be formed from three ring pieces that when arranged together form a ring shape. Magnetic ring assembly 76 is sized and shaped such that when it is positioned concentrically over actuator assembly 95, a gap of no less than 0.5 mm exists between an outer lateral surface of actuator assembly 95 and an interior surface of magnetic ring assembly 76.

Magnetic ring assembly 76 is concentrically positioned around actuator assembly 95 between first suspension ring 79 and second suspension ring 80, and is rigidly coupled to first suspension ring 79 and second suspension ring 80. Magnetic ring assembly 76 is rigidly coupled to the suspension rings by more than one post 81 spaced evenly around actuator assembly 95 and configured to extend parallel to a central axis of pump assembly 70. Suspension rings 79 and 80 and magnetic ring assembly 76 may be engaged such that magnetic ring assembly 76 is suspended equidistant between first electromagnetic coil 77 and second electromagnetic coil 78 when the suspension rings are in their non-deflected shapes. Each of suspension rings 79 and 80 and magnet ring holder portions 89 and 90 may include post receiving regions for engaging with posts 81 or may be affixed to posts 81 in any suitable manner that causes suspension rings 79 and 80 and magnetic ring assembly 76 to be rigidly affixed to posts 81. Posts 81 may extend beyond suspension rings 79 and 80 to engage other components, such as membrane assembly 82.

First electromagnetic coil 77 may be activated by controller applying an electrical signal from battery 40 to first electromagnetic coil 77, thus inducing current in the electromagnetic coil and generating a magnetic field surrounding electromagnetic coil 77. The direction of the current in electromagnetic coil 77 and the polarity of magnetic ring assembly 76 nearest electromagnetic coil 77 may be configured such that the first electromagnetic coil magnetically attracts or repels magnetic ring assembly 76 as desired. Similarly, a magnetic field may be created in second electromagnetic coil 78 by introducing a current in the second electromagnetic coil. The direction of the current in second electromagnetic coil 78 and the polarity of magnetic ring assembly 76 nearest the second electromagnetic coil also may be similarly configured so that first electromagnetic coil 77 magnetically attracts or repels magnetic ring assembly 76 when an appropriate current is induced in second electromagnetic coil 78.

Because magnetic ring assembly 76 is rigidly affixed to posts 81, which in turn are rigidly affixed to first suspension ring 79 and second suspension ring 80, the elastic properties of the suspension rings permit magnetic ring assembly 76 to move up towards first electromagnetic coil 77 or down towards second electromagnetic coil 78, depending upon the polarity of magnetic fields generated by the electromagnetic coils. In this manner, when magnetic ring assembly 76 experiences an upward magnetic force, magnetic ring assembly 76 deflects upward towards first electromagnetic coil 77. As posts 81 move upward with magnetic ring assembly 76, posts 81 cause the suspension rings 79 and 80 to elastically deform, which creates a spring force opposite to the direction of movement. When the magnetic field generated by the first electromagnetic coil collapses, when the electrical current ceases, this downward spring force causes the magnetic ring assembly to return to its neutral position. Similarly, when magnetic ring assembly 76 is magnetically attracted downward, magnetic ring assembly 76 deflects downward towards second electromagnetic coil 78. As posts 81 move downward with magnetic ring assembly 76, posts 81 impose an elastic deformation of the first and second suspension rings, thus generating a spring force in the opposite direction. When the magnetic field generated by the second electromagnetic coils collapses, when the electrical current ceases, this upward spring force causes the magnetic ring assembly to again return to its neutral position.

Electromagnetic coils 77 and 78 may be energized separately, or alternatively, may be connected in series to cause the electromagnetic coils to be activated simultaneously. In this configuration, first magnetic coil may be configured to experience a current flow direction opposite that of the second electromagnetic coil. Accordingly, when current is induced to first electromagnetic coil 77 to attract magnetic ring assembly 76, the same current is applied to second electromagnetic coil 78 to induce a current that causes second electromagnetic coil 78 to repel magnetic ring assembly 76. Similarly, when current is induced to second electromagnetic coil 78 to attract magnetic ring assembly 76, the current applied to first electromagnetic coil 77 causes the first electromagnetic coil to repel magnetic ring assembly 76. In this manner, electromagnetic coils 77 and 78 work together to cause deflection of magnetic ring assembly 76.

By manipulating the timing and intensity of the electrical signals applied to the electromagnetic coils, the frequency at which magnetic ring assembly 76 deflects towards the first and second electromagnetic coils may be altered. For example, by alternating the current induced in the electromagnetic coils more frequently, the magnetic ring assembly may be caused to cycle up and down more times in a given period. By increasing the amount of current, the magnetic ring assembly may be deflected at a faster rate and caused to travel longer distances.

Alternatively, first electromagnetic coil 77 and second electromagnetic coil 78 may be energized independently. For example, first electromagnetic coil 77 and second electromagnetic coil 78 may be energized at varying intensities; one may be coordinated to decrease intensity as the other increases intensity. In this manner, intensity of the signal applied to second electromagnetic coil 78 to cause downward magnetic attraction may simultaneously be increased as the intensity of the signal applied to first electromagnetic coil 77 causes an upward magnetic attraction that decreases.

In accordance with one aspect of the invention, movements of magnetic ring assembly 76 are translated to membrane assembly 82 which is disposed concentrically below stator assembly 72. Membrane assembly 82 preferably is rigidly attached to magnetic ring assembly 76 by posts 81.

Posts 81 may extend beyond second suspension ring 80 and may be coupled to membrane assembly 82.

Figure 17:
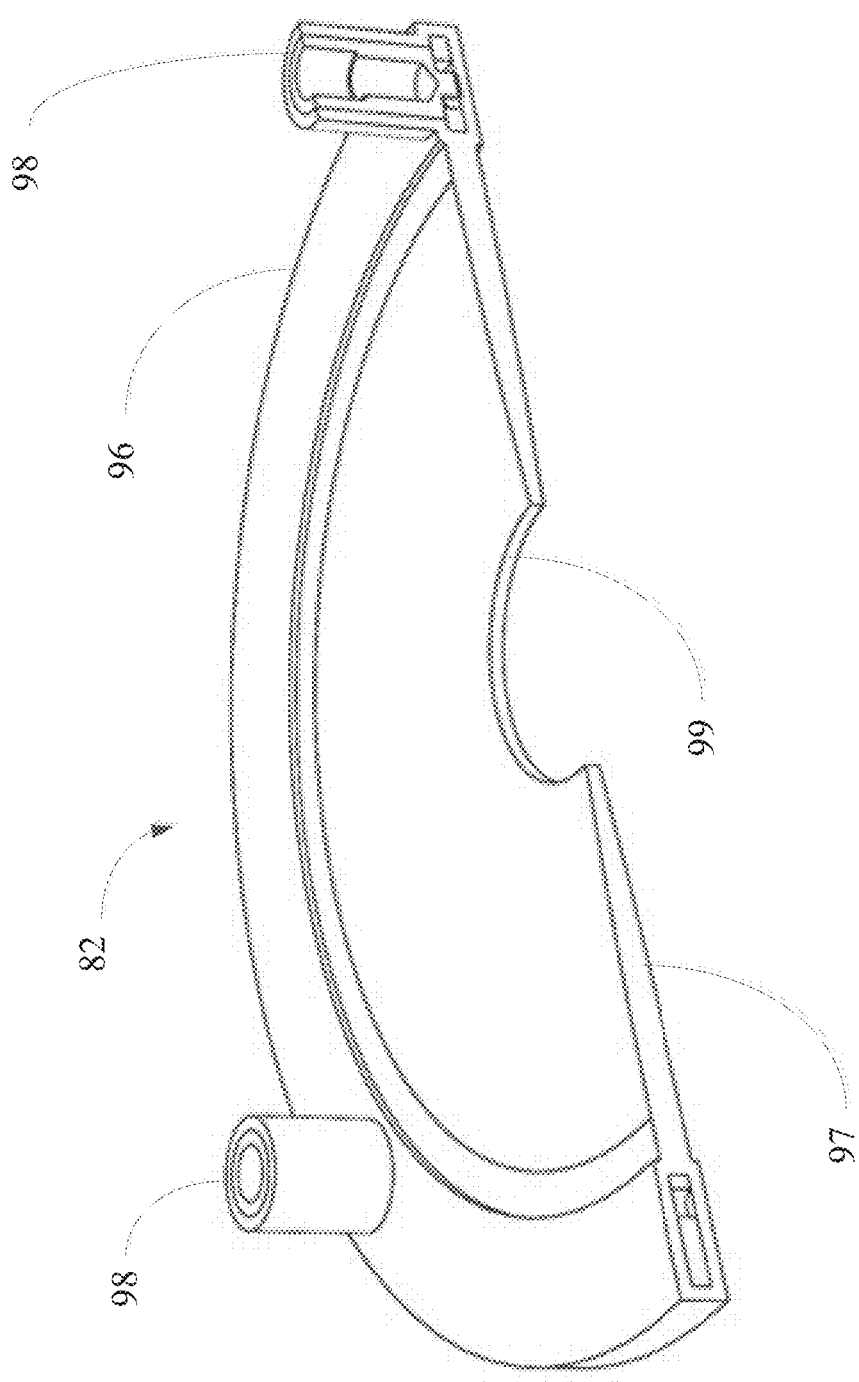
FIG. 17 is a perspective cross sectional view of the membrane assembly of the present invention.

Referring now to FIG. 17, membrane assembly 82 is described in greater detail. Membrane assembly 82 comprises rigid membrane ring 96 and membrane 97. Rigid membrane ring 96 exhibits rigid properties under typical forces experienced during the full range of operation of the present invention. Post reception sites 98 may be formed into rigid membrane ring 96 to engage membrane assembly 82 with posts 81. Alternatively, posts 81 may be attached to rigid membrane ring 96 in any other way which directly translates the motion of magnetic ring assembly 76 to rigid membrane ring 96. Rigid membrane ring 96 is affixed to membrane 97 and holds the membrane in tension. Membrane 97 may be molded directly onto rigid membrane ring 96 or may be affixed to rigid membrane ring 96 in any way that holds membrane 97 uniformly in tension along its circumference. Membrane 97 alternatively includes a flexible pleated structure where it attaches to rigid membrane ring 96 to increase the ability of the membrane to move where the membrane is affixed to rigid membrane ring 96. Membrane 97 further includes circular aperture 99 disposed in the center of the membrane.

In a preferred embodiment, membrane 97 has a thin, planar shape and is made of an elastomer having elastic properties and good durability. Alternatively, membrane 97 may have a uniform thickness from the membrane ring to the circular aperture. As a yet further alternative, membrane 97 may vary in thickness and exhibit more complex geometries. For example, as shown in FIG. 10, membrane 97 may have a reduced thickness as the membrane extends from rigid membrane ring 96 to circular aperture 99. Alternatively, or in addition to, membrane 97 may incorporate metallic elements such as a spiral spring to enhance the spring force of the membrane in a direction normal to plane of the membrane, and this spring force may vary radially along the membrane. In yet another embodiment, membrane 97 may be pre-formed with an undulating shape.

Figure 18:
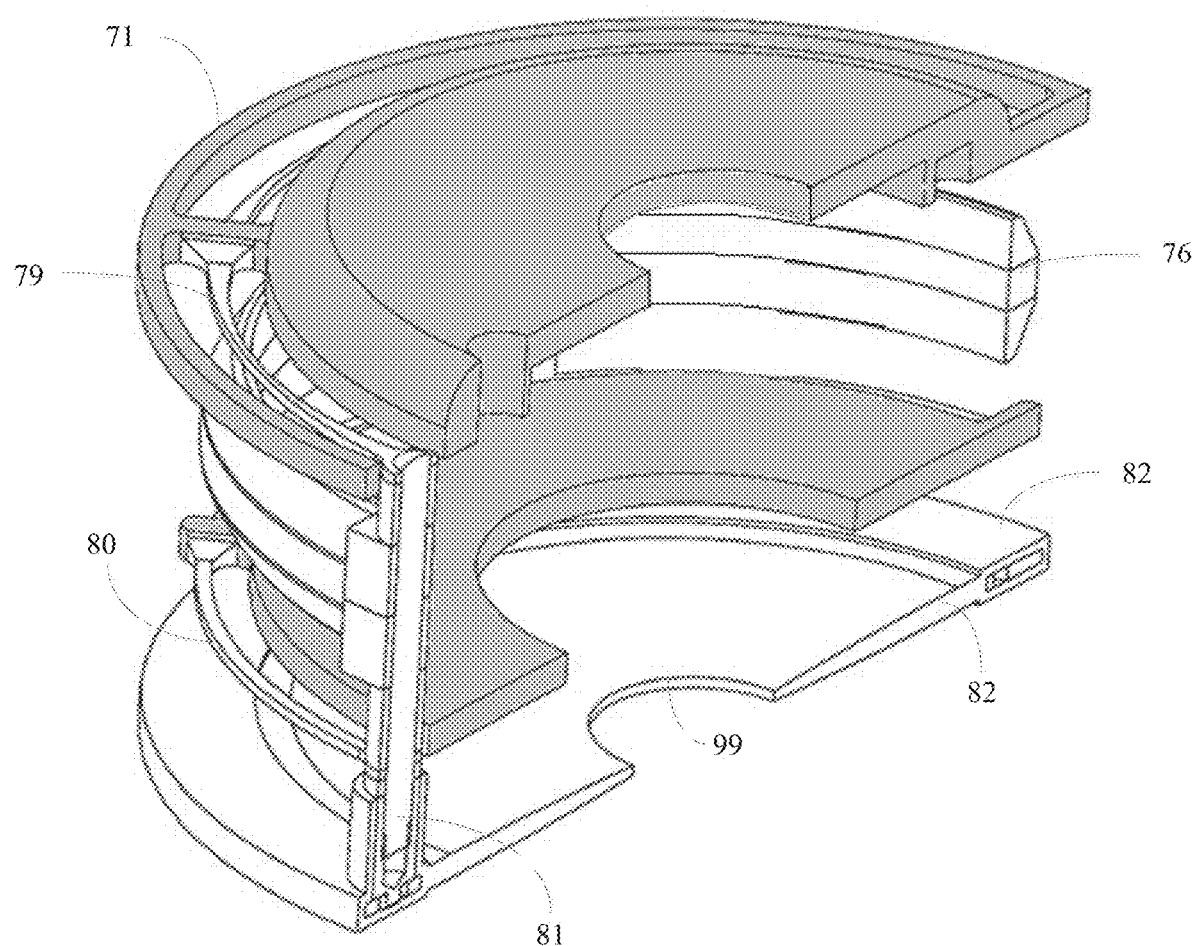
FIG. 18 is a perspective cross section view of the moving components of the pump assembly of the present invention.

FIG. 18 depicts moving portions of pump assembly 70 as non-grayed out elements. Non-moving portions of the pump assembly, i.e. actuator assembly 95 (partially shown), are fixed to pump housing 27 by fixation ring 71. Moving portions of pump assembly 70 include posts 81, first suspension spring 79, magnetic ring assembly 76, second suspension spring 80 and membrane assembly 82. As magnetic ring assembly 76 moves up and down, the movement is rigidly translated by posts 81 to membrane assembly 82. Given the rigidity of the posts, when magnetic ring assembly 76 travels a certain distance upward or downward, membrane assembly 82 travels the same distance. For example, when magnetic ring assembly 76 travels 4 mm from a position near first electromagnetic coil 77 to a position near second electromagnetic coil 78, membrane assembly 82 also travels 4 mm in the same direction. Similarly, the frequency at which magnetic ring assembly 76 traverses the space between the first and second electromagnetic coils is the same frequency at which membrane assembly 82 travels the same distance.

Figure 19:
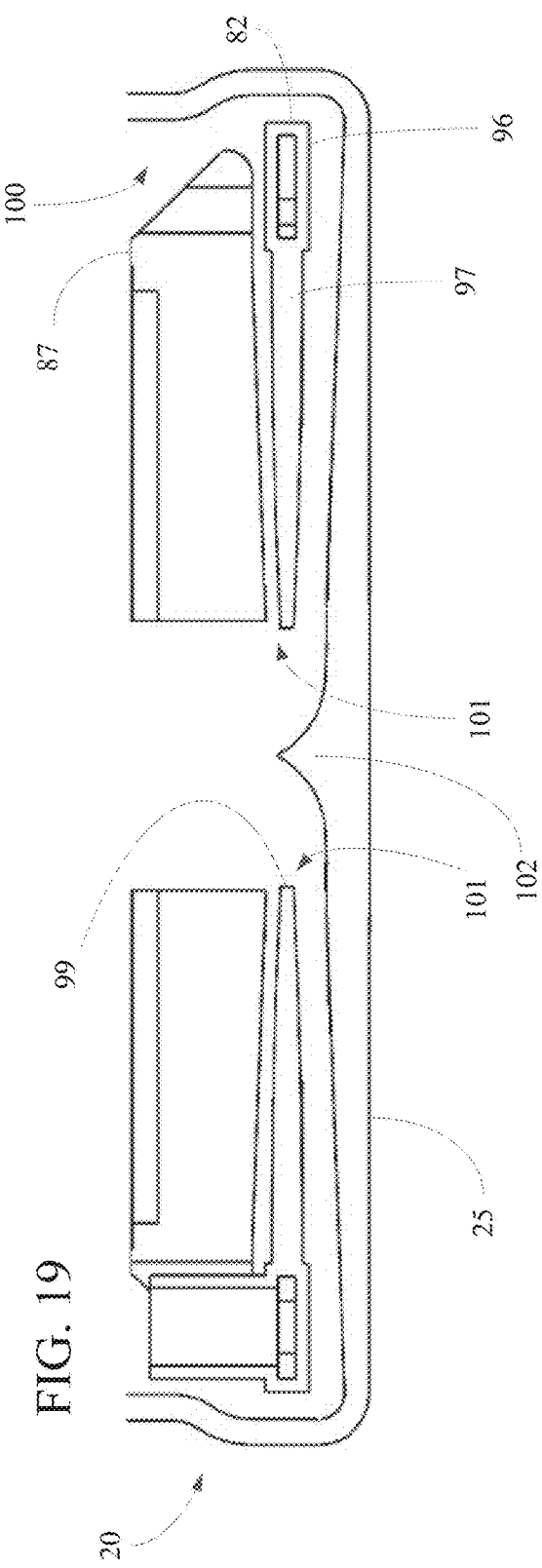
FIG. 19 is a cross sectional view of a lower portion of the implantable pump depicting the flow channel and membrane assembly in a resting position.

In accordance with one aspect of the present invention, the undulating membrane pump described herein avoids thrombus formation by placing all moving parts directly within the primary flow path, thereby reducing the risk of flow stagnation. Flow stagnation is further avoided by eliminating secondary flow paths that may experience significantly slower flow rates. Moving portions depicted in FIG. 18, including magnetic ring assembly 76, suspension rings 79 and 80, posts 81 and membrane assembly 82 are all located within delivery channel 100, defined by the interior surface of pump housing 27 and exterior of pump assembly 70, and flow channel 101, defined by a bottom surface of flanged portion 87 and the interior surface of lower housing portion 25. As is illustrated in FIGS. 6 and 19, blood enters implantable pump 20 from the left ventricle through inflow cannula 21 and flows downward along pump assembly 70 into delivery channel 100 which begins at the top of tapered section 83, extends to the area between pump housing 27 and actuator assembly 95, and finally extends down to flanged portion 87 of stator assembly 72 where blood enters delivery channel 100. By directing blood from inflow cannula 21 through delivery channel 100 to flow channel 101, delivery channel 100 delivers blood to membrane assembly 82.

Figure 20:
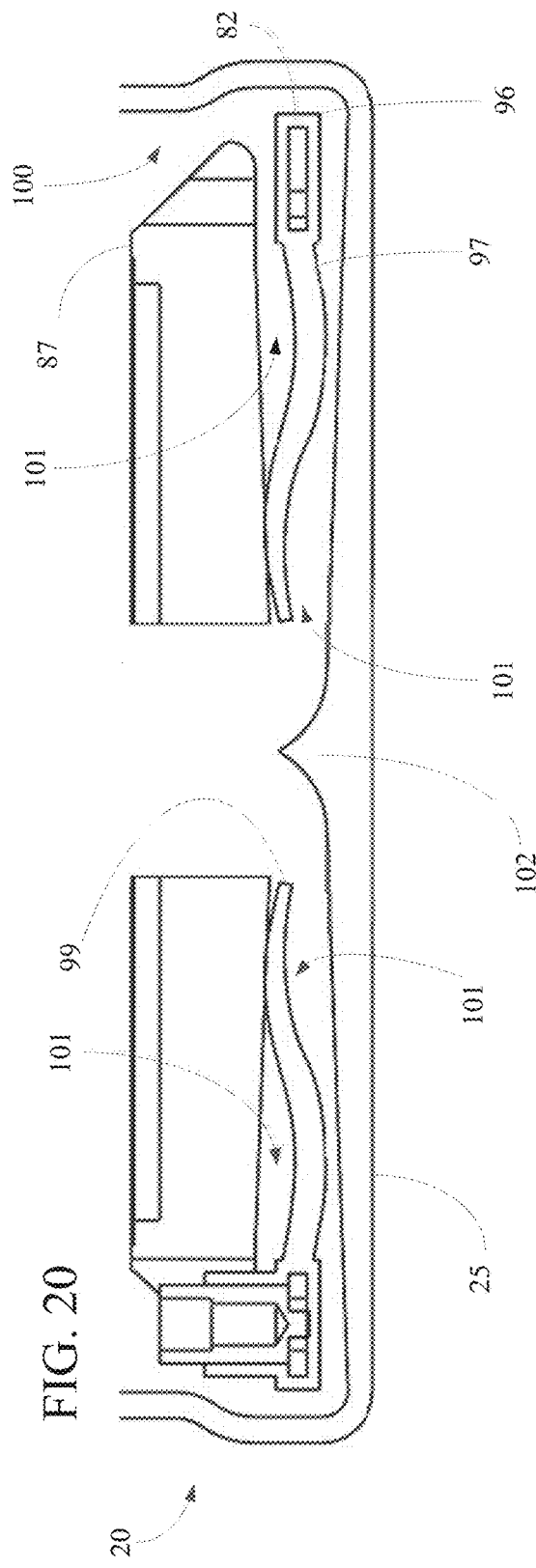
FIG. 20 is a cross sectional view of a lower portion of the implantable pump depicting the flow channel and membrane assembly with the membrane undulating.

Referring now to FIGS. 19 and 20, a lower portion of implantable pump 20, including flanged portion 87, membrane assembly 82 and lower housing portion 25 is shown. As is illustrated in FIG. 19, delivery channel 100 is in fluid communication with membrane assembly 82 and flow channel 101. Lower housing portion 25 may comprise feature 102 that extends upward as lower housing portion 25 moves radially inward. The interior surface of lower housing portion 25 may slope upward as it extends radially inward. Similarly, the bottom surface of flanged portion 87 may slope downward as it extends radially inward. The combination of the upward slope of the interior surface of lower housing portion 25 and the bottom surface of flanged portion 87 moving downward narrows flow channel 101 as the channel moves radially inward from delivery channel 100 to circular aperture 99 of membrane 97.

Membrane assembly 82 is suspended by posts 81 within flow channel 101 below the bottom surface of flanged portion 87 and above the interior surface of lower housing portion 25. Membrane assembly 82 is free to move up and down in the vertical direction within flow channel 101, which movement is constrained only by suspension rings 79 and 80. Membrane assembly 82 is constrained by rigid posts 81 and the suspension rings from twisting, tilting or moving in any direction in flow channel 101 other than up and down.

Flow channel 101 is divided by membrane 97 into an upper flow channel and a lower flow channel. The geometry of membrane 97 may be angled such that when membrane assembly 82 is at rest, the top surface of membrane 97 is parallel to the bottom surface of flanged portion 87 and the bottom surface of membrane 97 is parallel to the opposing surface of lower housing portion 25. Alternatively, membrane 97 may be sized and shaped such that when membrane assembly 82 is at rest, the upper and lower flow channels narrow as they move radially inward from delivery channel 100 to circular aperture 99 in membrane 97.

Referring now to FIG. 20, as rigid membrane ring 96 is caused by posts 81 to move up and down in flow channel 101, the outermost portion of membrane 97 nearest rigid membrane ring 96, moves up and down with rigid membrane ring 96. Membrane 97, being flexible and having elastic properties, gradually translates the up and down movement of the membrane portion nearest rigid membrane ring 96 along membrane 97 towards circular aperture 99. This movement across flexible membrane 97 causes wave-like deformations in the membrane which propagate inwards from rigid membrane ring 96 towards aperture 99.

The waves formed in the undulating membrane may be manipulated by changing the speed at which rigid membrane ring 96 moves up and down as well as the distance rigid membrane ring 96 moves up and down. As explained above, the amplitude and frequency at which rigid membrane ring 96 moves up and down is determined by the amplitude and frequency at which magnetic ring assembly 76 reciprocates over electromagnet assembly 91. Accordingly, the waves formed in the undulating membrane may be adjusted by changing the frequency and amplitude at which magnetic ring assembly 76 is reciprocated.

When blood is introduced into flow channel 101 from delivery channel 100, the undulations in membrane 97 cause blood to be propelled toward circular aperture 99 and out of pump housing 27 via outflow cannula 23. The transfer of energy from the membrane to the blood is directed radially inward along the length of the membrane towards aperture 99, and propels the blood along the flow channel towards outflow cannula 23 along both sides of membrane 97.

FIG. 20 shows that when rigid membrane ring 96 moves downward in unison with magnetic ring assembly 76, the upper portion of flow channel 101 near delivery channel 100 expands, causing blood from delivery channel 100 to fill the upper portion of the flow channel near the outer region of membrane 97. As rigid membrane ring 96 moves upward, the upper portion of flow channel 101 begins to narrow near rigid membrane ring 96, causing wave-like deformations to translate across the membrane. As the wave propagates across membrane 97, blood in the upper portion of flow channel 101 is propelled towards circular aperture and ultimately out of implantable pump 20 through outlet 22. Simultaneously, as rigid membrane ring 96 moves upwards, the lower portion of flow channel 101 nearest the outer portion of membrane 97 begins to enlarge, allowing blood from delivery channel 100 to flow into this region. Subsequently, when rigid membrane ring 96 is again thrust downwards, the region of flow channel 101 nearest outer portion of membrane 97 begins to narrow, causing wave-like deformations to translate across the membrane and propel blood towards outlet 22.

By manipulating the waves formed in the undulating membrane by changing the frequency and amplitude at which magnetic ring assembly 76 moves up and down, the pressure gradient within flow channel 101 and ultimately the flow rate of the blood moving through flow channel 101 may be adjusted. Appropriately controlling the movement of magnetic ring assembly 76 permits oxygen-rich blood to be effectively and safely pumped from the left ventricle to the aorta and throughout the body as needed.

In addition to merely pumping blood from the left ventricle to the aorta, implantable pump 20 of the present invention may be operated to closely mimic physiologic pulsatility, without loss of pump efficiency. Pulsatility may be achieved nearly instantaneously by changing the frequency and amplitude at which magnetic ring assembly 76 moves, to create a desired flow output, or by ceasing movement of the magnetic ring assembly for a period time to create a period of low or no flow output. Unlike typical rotary pumps, which require a certain period of time to attain a set number of rotations per minute to achieve a desired fluid displacement and pulsatility, implantable pump 20 may achieve a desired flow output nearly instantaneously and similarly may cease output nearly instantaneously due to the very low inertia generated by the small moving mass of the moving components of the pump assembly. The ability to start and stop on-demand permits rapid changes in pressure and flow. Along with the frequency and amplitude, the duty cycle, defined by the percentage of time membrane 97 is excited over a set period of time, may be adjusted to achieve a desired flow output and pulsatility, without loss of pump efficiency. Even holding frequency and amplitude constant, flow rate may be altered by manipulating the duty cycle between 0 and 100%.

In accordance with another aspect of the invention, controller 30 may be programmed by programmer 50 to operate at selected frequencies, amplitudes and duty cycles to achieve a wide range of physiologic flow rates and with physiologic pulsatilities. For example, programmer 50 may direct controller 30 to operate implantable pump 20 at a given frequency, amplitude and/or duty cycle during a period of time when a patient is typically sleeping and may direct controller 30 to operate implantable pump 20 at a different frequency, amplitude and or duty cycle during time periods when the patient is typically awake. Controller 30 or implantable pump also may include an accelerometer or position indicator to determine whether the patient is supine or ambulatory, the output of which may be used to move from one set of pump operating parameters to another. When the patient experiences certain discomfort or a physician determines that the parameters are not optimized, physician may alter one or more of at least frequency, amplitude and duty cycle to achieve the desired functionality. Alternatively, controller 30 or mobile device 60 may be configured to alter one or more of frequency, amplitude and duty cycle to suit the patient's needs.

Implantable pump 20 further may comprise one or more additional sensors for adjusting flow output and pulsatility according to the demand of the patient. Sensors may be incorporated into implantable pump 20 or alternatively or in addition may be implanted elsewhere in or on the patient. The sensors preferably are in electrical communication with controller 30, and may monitor operational parameters that measure the performance of implantable pump 20 or physiological sensors that measure physiological parameters of the patients such as heart rate or blood pressure. By using one or more physiological sensors, pulsatile flow may be synchronized with a cardiac cycle of the patient by monitoring blood pressure or muscle contractions, for example, and synchronizing the duty cycle according to the sensed output.

Controller 30 may compare physiological sensor measurements to current implantable pump output. If it is determined by analyzing sensor measurements that demand exceeds current output, frequency, amplitude and/or duty cycle may be automatically adjusted to meet current demand. Similarly, the controller may determine that current output exceeds demand and thus alter output by changing frequency, amplitude and/or duty cycle. Alternatively, or in addition to, when it is determined that demand exceeds current output, an alarm may sound from controller 30. Similarly, operational measurements from operational sensors may be compared against predetermined thresholds and where measurements exceed predetermined thresholds or a malfunction is detected, an alarm may sound from controller 30.

Implantable pump 20 is sized and shaped to produce physiological flow rates, pressure gradients and pulsatility at an operating point at which maximum efficiency is achieved. Specially, implantable pump 20 may be sized and shaped to produce physiological flow rates ranging from 4 to 6 liters per minute at pressure gradients lower than a threshold value associated with hemolysis. Also, to mimic a typical physiological pulse of 60 beats per minute, implantable pump 20 may pulse about once per second. To achieve such pulsatility, a duty cycle of 50% may be utilized with an "on" period of 0.5 seconds and an "off" period of 0.5 seconds. For a given system, maximum efficiency at a specific operating frequency, amplitude and voltage may be achieved while producing a flow rate of 4 to 6 liters per minute at a duty cycle of 50% by manipulating one or more of the shape and size of blood flow channels, elastic properties of the suspension rings, mass of the moving parts, membrane geometries, and elastic properties and friction properties of the membrane. In this manner, implantable pump 20 may be designed to produce desirable physiological outputs while continuing to function at optimum operating parameters.

By adjusting the duty cycle, implantable pump 20 may be configured to generate a wide range of output flows at physiological pressure gradients. For example, for an exemplary LVAD system configured to produce 4 to 6 liters per minute at a duty cycle of 50%, optimal operating frequency may be 120 Hz. For this system, flow output may be increased to 10 liters per minute or decreased to 4 liters per minute, for example, by changing only the duty cycle. As duty cycle and frequency operate independent of one another, duty cycle may be manipulated between 0 and 100% while leaving the frequency of 120 Hz unaffected.

The implantable pump system described herein, tuned to achieve physiological flow rates, pressure gradients and pulsatility, also avoids hemolysis and platelet activation by applying low to moderate shear forces on the blood, similar to those exerted by a healthy heart. The moving components are rigidly affixed to one another and do not incorporate any parts that would induce friction, such as mechanical bearings or gears. Delivery channel 100 is sized and configured to also avoid friction between moving magnetic ring assembly 76, suspension rings 79 and 80, posts 81 and lower housing portion 25 by sizing the channel such that clearances of at least 0.5 mm are maintained between all moving components. Similarly, magnetic ring assembly 76, suspension rings 79 and 80, and posts 81 all are offset from actuator assembly 95 by at least 0.5 mm to avoid friction between the actuator assembly and the moving parts.

Figure 21:
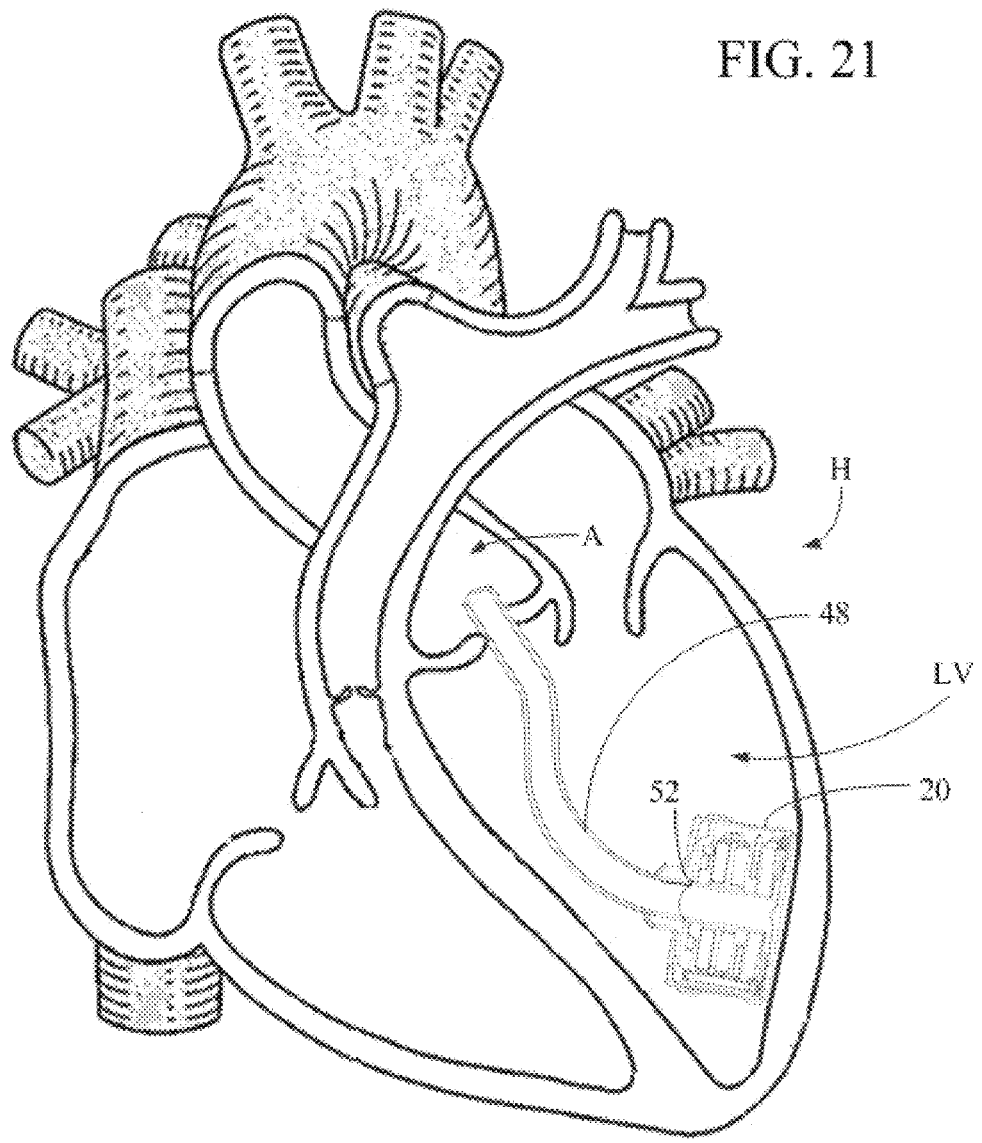
FIG. 21 is a sectional view of the implantable pump of the present invention implanted within the left ventricle having an outflow conduit extending into the aorta.

Referring now to FIG. 21, an alternative embodiment of implantable pump 20 is illustrated. As is shown in FIG. 21, implantable pump 20 may be sized and configured to be implanted within left ventricle LV of heart H. Implantable pump 20 may be similar to the implantable pump illustrated in FIGS. 2 and 6 but may have dimensions suitable for implantation within left ventricle LV. In this embodiment, implantable pump 20 may be secured to an interior wall of left ventricle LV along a bottom surface of implantable pump 20 or any other surface of implantable pump 20 suitable for securing implantable pump 20 to left ventricle LV. Implantable pump 20 may be secured using conventional techniques such as sutures. Inlet 28 of inflow cannula 21 may be sized and configured to maximize blood flow depending upon the orientation of implantable pump within left ventricle LV.

In this embodiment, implantable pump 20 may optionally include coupling section 52 for removably coupling outflow cannula 23 or outflow conduit 48 to coupling section 52 in the manner described above. In FIG. 21, outlet cannula 48 is illustrated extending from coupling section 52 into and through the aortic valve and into aorta A. In this manner, implantable pump 20 may pump blood from implantable pump 20 located within left ventricle LV, through the aortic valve and ultimately to aorta A via outflow conduit 48. As explained above, outflow conduit 48 may be flexible or semi-rigid. Accordingly, outlet conduit 48 may twist and conform to the contours of left ventricle the aortic valve and may extend through the aortic valve without causing damage to left ventricle LV, the aortic valve or aorta A.

In the embodiment illustrated in FIG. 21 where implantable pump 20 is implanted within left ventricle LV, cable 29 may extend through a small opening in heart H, or may extend through a chamber of heart H to supply an electrical signal to implantable pump 20. Alternatively, implantable pump 20 may include a battery and circuitry within pump housing 27 which may supply an electrical signal to implantable pump 20 at the direction of controller 30. The battery may be charged transcutaneously using battery 40 or other exterior battery configured to transcutaneously charge the battery within pump housing 27. Controller 30 may wirelessly communicate and control actuation of implantable pump 20. In this embodiment, controller 30 and battery 40 or other charging battery may be worn on a vest near heart H.

While various illustrative embodiments of the invention are described above, it will be apparent to one skilled in the art that various changes and modifications may be made therein without departing from the invention. For example, pump assembly 70 shown in FIG. 16 may be ordered differently and may include additional or fewer components of various sizes and composition. The appended claims are intended to cover all such changes and modifications that fall within the true spirit and scope of the invention.

What is claimed is:

1. An implantable cardiovascular pump system comprising,
a housing configured to be coupled to a patient's heart;
a pump assembly disposed within the housing, the pump assembly comprising an actuator assembly coupled to a circumference of a vibrating membrane, the vibrating membrane unsupported other than at the circumference;
an outflow cannula, the outflow cannula having an outlet disposed within a left ventricle of the patient's heart and an inlet in fluid communication with the pump assembly; and
an inflow cannula, the inflow cannula having an inlet disposed within the left ventricle of patient's heart and an outlet in fluid communication with the pump assembly,
wherein the actuator assembly is configured to cause the vibrating membrane to vibrate to transfer blood in a pulsatile manner from the inlet of the inflow cannula through the housing around the actuator assembly and out the outlet of the outflow cannula.

2. The implantable cardiovascular pump system of claim 1, wherein the outlet of the outflow cannula is oriented toward an aortic valve, and is also configured to direct fluid flow from the pump assembly to the aortic valve.

3. The implantable cardiovascular pump system of claim 1, wherein the actuator assembly is configured to cause the transfer of blood in the pulsatile manner such that pulsatile flow is synchronized with a cardiac cycle of the patient.

4. The implantable cardiovascular pump system of claim 3, further comprising one or more physiological sensors, wherein the actuator assembly is configured to cause the pulsatile flow that is synchronized based on sensed output from the one or more physiological sensors.

5. The implantable cardiovascular pump system of claim 4, wherein the one or more physiological sensors are configured to sense blood pressure or muscle contraction or both.

6. The implantable cardiovascular pump system of claim 1, further comprising an anchor coupled to the outflow cannula and configured to anchor the outflow cannula to a left ventricular outflow tract.

7. The implantable cardiovascular pump system of claim 1, wherein the inflow cannula and outflow cannula are coaxial.

8. The implantable cardiovascular pump system of claim 1, wherein the actuator assembly comprises a magnetic ring assembly configured to reciprocate and wherein the vibrating membrane is coupled to the magnetic ring assembly such that movement of the magnetic ring assembly causes movement of the membrane assembly.

9. The implantable cardiovascular pump system of claim 8, wherein the actuator assembly is configured to generate a pulsatile blood flow by performing one or more of changing a frequency at which the magnetic ring assembly moves, changing an amplitude at which the magnetic ring assembly moves or ceasing movement of the magnetic ring assembly for a period of time.

10. The implantable cardiovascular pump system of claim 8, wherein the actuator assembly further comprises a first electromagnetic coil and a second electromagnetic coil.

11. The implantable cardiovascular pump system of claim 10, wherein the actuator assembly is configured to activate the first electromagnetic coil to attract the magnetic ring assembly such that the magnetic ring assembly moves in an upward direction.

12. The implantable cardiovascular pump system of claim 11, wherein the actuator assembly is configured to activate the second electromagnetic coil to attract the magnetic ring assembly such that the magnetic ring assembly moves in a downward direction.

13. The implantable cardiovascular pump system of claim 1, wherein the vibrating membrane comprises an aperture, and wherein vibration of the vibrating membrane causes blood to flow along the vibrating membrane and towards the aperture.

14. The implantable cardiovascular pump system of claim 1, wherein the housing includes a surface having an opening resealably closed by a plug or a valve.

15. A method of pumping blood, the method comprising:
delivering blood through an inlet of an inflow cannula coupled to and in fluid communication with a housing, the inlet of the inflow cannula disposed within a left ventricle of a patient's heart;
directing blood through the housing to a pump assembly disposed within the housing, the pump assembly comprising an actuator assembly coupled to a flexible membrane at a first end of the flexible membrane;
exciting the actuator assembly to cause the first end of the flexible membrane to reciprocate to propagate a wave along the flexible membrane thereby propelling blood from a first end of the flexible membrane to a second end of the flexible membrane that is suspended in the housing;
directing blood in a pulsatile manner from an inlet of an outflow cannula in fluid communication with the second end of the flexible membrane to an outlet of the outflow cannula disposed within the left ventricle of the heart of the patient.

16. The method of claim 15, wherein the actuator assembly is configured to cause the transfer of blood in the pulsatile manner such that pulsatile flow is synchronized with a cardiac cycle of the patient.

17. The method of claim 16, further comprising one or more physiological sensors, wherein the actuator assembly is configured to cause the pulsatile flow that is synchronized based on sensed output from the one or more physiological sensors.

18. The method of claim 17, wherein the one or more physiological sensors are configured to sense blood pressure or muscle contraction or both.

19. The method of claim 15, wherein the actuator assembly comprises a magnetic ring assembly adapted to reciprocate and wherein the flexible membrane is coupled to the magnetic ring assembly such that movement of the magnetic ring assembly causes movement of the membrane assembly.

20. The method of claim 19, wherein the actuator assembly is configured to generate a pulsatile blood flow by performing one or more of changing a frequency at which the magnetic ring assembly moves, changing an amplitude at which the magnetic ring assembly moves or ceasing movement of the magnetic ring assembly for a period of time.

21. The method of claim 19, wherein the actuator assembly further comprises a first electromagnetic coil and a second electromagnetic coil.

22. The method of claim 21, wherein exciting the actuator assembly comprises activating the first electromagnetic coil to attract the magnetic ring assembly such that the magnetic ring assembly moves in an upward direction.

23. The method of claim 22, wherein exciting the actuator assembly further comprises activating the second electromagnetic coil to attract the magnetic ring assembly such that the magnetic ring assembly moves in a downward direction.

24. The method of claim 15, wherein delivering blood through an inlet of an inflow cannula comprises delivering blood in a first direction, and wherein directing blood from an inlet of an outflow cannula in fluid communication with the second end of the membrane to an outlet of the outflow cannula comprises delivering blood in a second direction, opposite of the first direction.

25. The method of claim 15, wherein the flexible membrane is circular and comprises an aperture disposed near the second end of the flexible membrane, and wherein movement of the flexible membrane causes blood to flow along the flexible membrane and towards the aperture.

26. The method of claim 15, wherein the outflow cannula is disposed coaxially within the inflow cannula.

27. The method of claim 15, wherein the outlet of the outflow cannula is oriented toward an aortic valve, and is also configured to direct fluid flow from the pump assembly to the aortic valve.

28. The method of claim 15, wherein the housing includes a surface having an opening resealably closed by a plug or a valve.

* * * * *